US010584161B2

(12) United States Patent
Calvert et al.

(10) Patent No.: US 10,584,161 B2
(45) Date of Patent: Mar. 10, 2020

(54) MONOCLONAL ANTIBODIES SPECIFIC FOR HEARTLAND VIRUS AND METHODS OF THEIR USE

(71) Applicant: The U.S.A., as represented by the Secretary, Deapartment of Health and Human Services, Bethesda, MD (US)

(72) Inventors: Amanda E. Calvert, Fort Collins, CO (US); Aaron C. Brault, Fort Collins, CO (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 77 days.

(21) Appl. No.: 15/761,789

(22) PCT Filed: Jan. 12, 2016

(86) PCT No.: PCT/US2016/013073
§ 371 (c)(1),
(2) Date: Mar. 20, 2018

(87) PCT Pub. No.: WO2017/052679
PCT Pub. Date: Mar. 30, 2017

(65) Prior Publication Data
US 2018/0244757 A1    Aug. 30, 2018

Related U.S. Application Data

(60) Provisional application No. 62/221,431, filed on Sep. 21, 2015.

(51) Int. Cl.
*C07K 16/10*     (2006.01)
*G01N 33/53*     (2006.01)
*G01N 33/569*    (2006.01)
*A61K 39/00*     (2006.01)
*A61K 39/12*     (2006.01)

(52) U.S. Cl.
CPC ....... *C07K 16/10* (2013.01); *G01N 33/56983* (2013.01); *A61K 39/12* (2013.01); *A61K 2039/505* (2013.01); *C07K 2317/21* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/624* (2013.01); *C07K 2317/76* (2013.01); *C07K 2319/00* (2013.01); *C12N 2760/12211* (2013.01); *G01N 2333/175* (2013.01); *G01N 2469/20* (2013.01)

(58) Field of Classification Search
None
See application file for complete search history.

(56) References Cited

PUBLICATIONS

Calvert et al., "Development and Characterization of Monoclonal Antibodies Directed against the Nucleoprotein of Heartland Virus," *Am. J. Trop. Med. Hyg.*, vol. 93:1338-1340, 2015.
Calvert et al., "Heartland Virus Produces a Humoral Response Lacking Virus-Neutralizing Antibody *In Vivo*," poster presentation at Keystone Symposium—Viral Immunity, Breckenridge, Colorado, Jan. 11-16, 2015.
Calvert et al., "Heartland Virus Produces a Humoral Response Lacking Virus-Neutralizing Antibody *In Vivo*," Abstract submitted to Keystone Symposium—Viral Immunity, Breckenridge, Colorado, Jan. 11-16, 2015.
Fafetine et al., "Generation and Characterization of Monoclonal Antibodies Against Rift Valley Fever Virus Nucleoprotein," *Transbound. Emerg. Dis.*, vol. 60:24-30, 2013.
Martin-Folgar et al., "Development and Characterization of Monoclonal Antibodies against Rift Valley Fever Virus Nucleocapsid Protein Generated by DNA Immunization," *mAbs*, vol. 2:275-284, 2010.
McMullan, et al., "A New Phlebovirus Associated with Severe Febrile Illness in Missouri," *N. Engl. J. Med.*, vol. 367:834-841, 2012.
Muehlenbachs, et al., "Heartland Virus-Associated Death in Tennessee," *Clin. Infect. Dis.*, vol. 59:845-850, 2014.
Yu et al., "Application of Recombinant Severe Fever with Thrombocytopenia Syndrome Virus Nucleocapsid Protein for the Detection of SFTSV-Specific Human IgG and IgM Antibodies by Indirect ELISA," *Virol., J.*, vol. 12:117, 2015.

*Primary Examiner* — Stacy B Chen
(74) *Attorney, Agent, or Firm* — Klarquist Sparkman, LLP

(57) ABSTRACT

Monoclonal antibodies that specifically bind the nucleocapsid protein of Heartland virus (HRTV) are described. The monoclonal antibodies can be used, for example, in immunoassays to detect HRTV-specific antibodies in a biological sample or to detect HRTV in a cell or tissue sample. The monoclonal antibodies can also be used to diagnose or treat an HRTV infection.

24 Claims, 5 Drawing Sheets

Specification includes a Sequence Listing.

FIG. 3A Heartland virus diagnostic comparisons

| Patient | DPO[1] | RNA/VI | IgM-MIA[2] | IgM MIA P/N | IgM-IFA[3] | IgG-MIA[2] | MIA IgG P/N | IgG ELISA P/N | HRT PRNT | Interpretation |
|---|---|---|---|---|---|---|---|---|---|---|
| 1 | 7 | Neg VI&RNA | n/t[4] | n/t | n/t | n/t | n/t | n/t | n/t | past HRTL infection |
|   | 7 |  | 49 | 1.9 | neg | 5479 | 158.1 | 4 | 20 |  |
|   | 37 |  | 84 | 3.2 | neg | 8342 | 240.6 | 16.5 | 80 |  |
| 2 | 11 | Neg VI | n/t | n/t | n/t | n/t | n/t | n/t | n/t | current HRTL infection |
|   | 11 |  | n/t | n/t | 0 | n/t | n/t | * | 10 |  |
|   | 31 |  | 1800 | 68.4 | >64 | 8087 | 233.3 | 4.9 | 640 |  |
|   | 95 |  | 1024 | 38.9 | >64 | 8525 | 245.9 | 3.6 | 640 |  |
| 3 | 4 | Neg VI | n/t | n/t | n/t | n/t | n/t | n/t | n/t | past HRTL infection |
|   | 4 | Neg VI | 113 | 4.3 | neg | 3101 | 89.5 | * | 20 |  |
| 4 | 21 | Neg RNA | n/t | n/t | n/t | n/t | n/t | n/t | n/t | past HRTL infection |
|   | 21 |  | 14 | 0.6 | neg | 6338 | 182.8 | 1.9 | 40 |  |
|   | 49 |  | 16 | 0.6 | neg | 4934 | 142.3 | 2.4 | 40 |  |
| 5 | 22 | Neg RNA | n/t | n/t | n/t | n/t | n/t | n/t | n/t | current HRTL infection |
|   | 22 |  | 1668 | 63.4 | 16 | 7156 | 206.4 | 14.2 | 320 |  |
|   | 48 |  | 1098 | 41.7 | 8 | 8727 | 251.7 | 20.6 | 1280 |  |
|   | 90 |  | 747 | 28.4 | 8 | 8644 | 249.4 | 3.5 | 1280 |  |
| 6 | 7 |  | n/t | n/t | n/t | n/t | n/t | n/t | n/t | past HRTL infection |
|   | 7 |  | 24 | 0.9 | neg | 3392 | 97.9 | 6.8 | 20 |  |
|   | 15 |  | 22 | 0.8 | neg | 3946 | 113.8 | 7.5 | 20 |  |
|   | 25 |  | 25 | 1 | neg | 5124 | 147.8 | 6.3 | 20 |  |
| 7 | 10 | Neg RNA | n/t | n/t | n/t | n/t | n/t | n/t | n/t | past HRTL infection |
|   | 10 |  | 25 | 1 | neg | 6718 | 193.8 | 2 | 40 |  |
|   | 63 |  | 81 | 3.1 | neg | 7752 | 223.6 | 5.6 | 80 |  |
| 8 | 6 | Neg RNA | n/t | n/t | n/t | n/t | n/t | n/t | n/t | past HRTL infection |
|   | 6 |  | 32 | 1.2 | neg | 6467 | 186.6 | 3.9 | 20 |  |
|   | 103 |  | 26 | 1 | neg | 7411 | 213.8 | 5.3 | 20 |  |

FIG. 3B

| Patient | DPO[1] | RNA/VI | IgM-MIA[2] | IgM MIA P/N | IgM-IFA[3] | IgG-MIA[1] | MIA IgG P/N | IgG ELISA P/N | HRT PRNT | Interpretation |
|---|---|---|---|---|---|---|---|---|---|---|
| 9 | 4 | Neg RNA | n/t | n/t | n/t | n/t | n/t | n/t | n/t | current HRTL infection |
|   | 4 |  | 855 | 32.5 | >64 | 6349 | 183.2 | 6.8 | 40 |  |
|   | 37 |  | 1241 | 47.1 | 32 | 8537 | 246.3 | 7.1 | 160 |  |
| 10 | 4 | Pos RNA | n/t | n/t | n/t | n/t | n/t | n/t | n/t | current HRTL infection |
|    | 4 |  | 197 | 7.6 | neg | 132 | 3.3 | 1 | <10 |  |
|    | 38 |  | n/t | n/t | n/t | n/t | n/t | * | >320 |  |
| 11 | 5 | Pos RNA | n/t | n/t | n/t | n/t | n/t | n/t | n/t | current HRTL infection |
|    | 5 |  | n/t | n/t | n/t | n/t | n/t | 0.82 | <10 |  |
|    | 35 |  | 2624 | 101.6 | 16 | 11419 | 290.3 | * | >160 |  |
| 12 | 9 | Pos RNA | n/t | n/t | n/t | n/t | n/t | n/t | n/t | current HRTL infection |
|    | 12 |  | 229 | 8.9 | neg | 147 | 3.7 | 1.2 | <10 |  |
| 13 | 14 | Neg RNA | n/t | n/t | n/t | n/t | n/t | n/t | n/t | past HRTL infection |
|    | 14 |  | 36 | 1.1 | neg | 3582 | 43.9 | 1.5 | 10 |  |
|    | 38 |  | 78 | 2.5 | neg | 5061 | 62 | 2.1 | <10[5] |  |
| 14 | 7 | Equiv RNA | n/t | n/t | n/t | n/t | n/t | n/t | n/t | current HRTL infection |
|    | 7 |  | n/t | n/t | n/t | n/t | n/t | 1 | <10 |  |
|    | 26 |  | 1513 | 57.5 | 16 | 6711 | 193.6 | 1.1 | 320 |  |
| 15 | 8 | Pos RNA | n/t | n/t | n/t | n/t | n/t | n/t | n/t | current HRTL infection |
|    | 8 |  | 39 | 1.5 | neg | 80 | 2 | 0.76 | <10 |  |
|    | 25 |  | 700 | 27.1 | 8 | 5987 | 152.2 | 3.5 | >320 |  |
| 16 | 15 | Pos RNA/neg VI | n/t | n/t | n/t | n/t | n/t | n/t | n/t | current HRTL infection |
|    | 15 |  | n/t | n/t | n/t | n/t | n/t | 0.59 | <10 |  |
| 17 | 5 | Pos RNA | n/t | n/t | n/t | n/t | n/t | n/t | n/t | current HRTL infection |
|    | 5 |  | 538 | 21.3 | 8 | 8609 | 217 | 0.35 | <10 |  |
|    | 95 |  | n/t | n/t | n/t | n/t | n/t | 19.6 | 640 |  |
| 18 | 8 | Pos RNA | n/t | n/t | n/t | n/t | n/t | n/t | n/t | current HRTL infection |
|    | 8 |  | 1432 | 56.5 | 16 | 7201 | 181.4 | 0.58 | <10 |  |
|    | 95 |  | n/t | n/t | n/t | n/t | n/t | 14.6 | 160 |  |

FIG. 3C

| Patient | DPO[1] | RNA/VI | IgM-MIA[2] | IgM MIA P/N | IgM-IFA[3] | IgG-MIA[1] | MIA IgG P/N | IgG ELISA P/N | HRT PRNT | Interpretation |
|---|---|---|---|---|---|---|---|---|---|---|
| 19 | 12 | Pos RNA | n/t | n/t | n/t | n/t | n/t | n/t | n/t | current HRTL infection |
|    | 12 | n/t | 2215 | 85.8 | 8 | 2640 | 67.1 | 0.34 | <10 | |
| 20 | 11 | Neg RNA | n/t | n/t | n/t | n/t | n/t | n/t | n/t | past HRTL infection |
|    | 11 | n/t | 57 | 1.8 | neg | 4174 | 51.1 | 1.7 | 10 | |
|    | 58 | n/t | 133 | 4.3 | neg | 6643 | 81.3 | 19.9 | 40 | |
| 21 | 3 | Neg RNA | n/t | n/t | n/t | n/t | n/t | n/t | n/t | current HRTL infection |
|    | 3 | n/t | n/t | n/t | n/t | n/t | n/t | 1.3 | <10 | |
|    | 21 | n/t | 1993 | 64.3 | >64 | 760 | 9.3 | 1.7 | <10 | |
| 22 | 22 | Equiv RNA | n/t | n/t | n/t | n/t | n/t | n/t | n/t | current HRTL infection |
|    | 22 | n/t | 10266 | 389.9 | >64 | 5130 | 148 | 1.1 | 80 | |
|    | 86 | n/t | 9304 | 367.3 | >64 | 9799 | 247.1 | 14.6 | 320 | |
| 23 | 4 | Neg RNA | n/t | n/t | n/t | n/t | n/t | n/t | n/t | current HRTL infection |
|    | 4 | n/t | 1118 | 43.3 | >64 | 1224 | 31.1 | 0.46 | <10 | |
|    | 31 | n/t | 6903 | 267.2 | >64 | 9099 | 231.3 | 1.9 | 1280 | |
| 24 | 11 | Pos RNA | n/t | n/t | n/t | n/t | n/t | n/t | n/t | current HRTL infection |
|    | 11 | n/t | 4304 | 14.8 | 32 | 2449 | 62.3 | 0.73 | <10 | |

MONOCLONAL ANTIBODIES SPECIFIC FOR HEARTLAND VIRUS AND METHODS OF THEIR USE

CROSS REFERENCE TO RELATED APPLICATIONS

This application is the U.S. National Stage of International Application No. PCT/US2016/13073, filed Jan. 12, 2016, published in English under PCT Article 21(2), which claims the benefit of U.S. Provisional Application No. 62/221,431, filed Sep. 21, 2015, which is herein incorporated by reference in its entirety.

FIELD

This disclosure concerns monoclonal antibodies that specifically recognize Heartland virus (HRTV), and diagnostic assays for detecting HRTV using the disclosed antibodies.

BACKGROUND

The genus *Phlebovirus* is one of five genera of the Bunyaviridae family. Phleboviruses are enveloped spherical viruses with icosahedral symmetry. The genome of phleboviruses consists of three single-stranded RNA genome segments—small (S), medium (M) and large (L). The M and L segments use a negative sense coding strategy, while the S segment encodes two proteins using an ambisense strategy. The S segment encodes the non-structural protein NSs in the positive sense orientation and the nucleocapsid (N) protein in the negative sense orientation; each protein is translated from a subgenomic virus mRNA. The M segment encodes the glycoprotein precursor that is cleaved by host proteases into two structural domains—Gn and Gc. The L segment encodes the L protein, which functions as the RNA-dependent RNA polymerase in primary and secondary transcription to generate mRNA and replicative intermediates, respectively.

Heartland virus (HRTV) is a newly identified member of the *Phlebovirus* genus. It was first isolated from leukocytes of two Missouri farmers in separate incidences hospitalized in 2009 (McMullan et al., *N Engl J Med* 367: 834-841, 2012; PCT Publication No. WO 2013/142808). Each subject experienced similar, though not identical symptoms of fever, headache, anorexia, gastrointestinal distress and fatigue, and both reported recent tick bites. Initial investigations for erhlichiosis and rickettsial diseases returned negative results, and EDTA-treated blood taken two days after hospital admission was taken for further investigation (McMullan et al., *N Engl J Med* 367: 834-841, 2012). After cytopathic effect without bacterial microcolonies was observed in cell culture approximately nine days post-inoculation, a viral infection was suspected. Thin-section electron microscopy revealed enveloped particles consistent in size with those of the Bunyaviridae family Next-generation sequencing and phylogenetic analysis confirmed the discovery of isolates of a novel bunyavirus of the genus *Phlebovirus*, which was subsequently named Heartland virus.

HRTV is believed to be transmitted to humans by the bite of an infected *Amblyomma americanum* tick (Savage et al., *Am J Trop Med Hyg* 89: 445-452, 2013). It causes severe disease characterized by fever, leukopenia and thrombocytopenia (McMullan et al., *N Engl J Med* 367: 834-841, 2012). HRTV is closely related to severe fever with thrombocytopenia virus (SFTSV), a phlebovirus causing severe disease in China and neighboring countries (Yu et al., *N Engl J Med* 364: 1523-1532, 2011.). SFTSV is also thought to be transmitted by ticks. The average case fatality rate of SFTSV infection is between 6-17% with the most severe manifestations occurring in elderly individuals (Xu et al., *PLoS Pathog* 7: e1002369, 2011).

SUMMARY

Monoclonal antibodies specific for HRTV are disclosed herein. The HRTV-specific monoclonal antibodies can be used, for example, for the diagnosis and treatment of HRTV infection.

Provided herein are isolated monoclonal antibodies specific for the nucleocapsid (N) protein of HRTV, or antigen-binding fragments thereof. In some embodiments, the variable heavy (VH) and variable light (VL) domains of the monoclonal antibody (or antigen-binding fragment) comprise the complementarity determining region (CDR) sequences of a monoclonal antibody disclosed herein (referred to as 2AF11, 2AG8, 2AG9, 2BA2, 2BB5, 2BB6, 2BB7, 2BB8 and 2BB10). Also provided herein are fusion proteins comprising a disclosed monoclonal antibody (or antigen-binding fragment) and a heterologous protein; immunoconjugates comprising a disclosed monoclonal antibody (or antigen-binding fragment) and a detectable label; compositions comprising a disclosed monoclonal antibody (or antigen-binding fragment) and a pharmaceutically acceptable carrier; and compositions comprising a disclosed monoclonal antibody (or antigen-binding fragment) conjugated to a microsphere.

Further provided are methods of detecting HRTV-specific antibodies in a biological sample. In some embodiments, the method is a microsphere immunoassay (MIA) that uses a disclosed monoclonal antibody (or antigen-binding fragment) conjugated to a microsphere. In other embodiments, the method is an indirect ELISA that uses a disclosed monoclonal antibody (or antigen-binding fragment) bound to a solid support, such as a microtiter plate. In yet other embodiments, the method is an antibody capture ELISA in which a labelled monoclonal antibody (or antigen-binding fragment) disclosed herein is used to detect immune complexes containing HRTV-specific antibodies from a biological sample.

Also provided herein are methods of detecting HRTV in an isolated cell or tissue by contacting the cell or tissue with a monoclonal antibody or immunoconjugate disclosed herein and detecting binding of the monoclonal antibody or immunoconjugate to the cell or tissue.

A method of treating HRTV infection in a subject by administering to the subject a monoclonal antibody or antigen-binding fragment (or immunoconjugate thereof) disclosed herein is also provided by the present disclosure.

Further provided are nucleic acid molecules and vectors encoding a disclosed monoclonal antibody or antigen binding fragment. Isolated host cells transformed with the nucleic acid molecules and vectors are also provided.

The foregoing and other objects, features, and advantages of the invention will become more apparent from the following detailed description, which proceeds with reference to the accompanying figures.

BRIEF DESCRIPTION OF THE DRAWINGS

FIGS. 3A-3C provide a table showing Heartland virus diagnostic comparisons.

SEQUENCE LISTING

Figure 1:
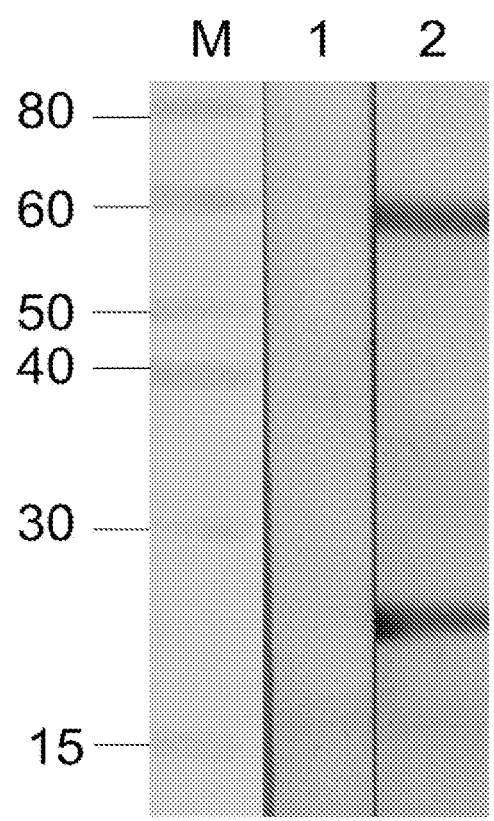
FIG. 1 is a blot showing reactivity of pooled mouse sera from day 34 post-infection. M, low-molecular mass marker (sizes are shown in KDa); Lane 1, mouse 1; Lane 2, mouse 2.

The nucleic acid and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 1, 2018, 28.4 KB, which is incorporated by reference herein. In the accompanying sequence listing:

SEQ ID NOs: 1 and 2 are the nucleotide and amino acid sequences of the 2AF11 VH domain.

SEQ ID NOs: 3 and 4 are the nucleotide and amino acid sequences of the 2AF11 VL domain.

SEQ ID NOs: 5 and 6 are the nucleotide and amino acid sequences of the 2AG8 VH domain.

SEQ ID NOs: 7 and 8 are the nucleotide and amino acid sequences of the 2AG8 VL domain.

SEQ ID NOs: 9 and 10 are the nucleotide and amino acid sequences of the 2AG9 VH domain.

SEQ ID NOs: 11 and 12 are the nucleotide and amino acid sequences of the 2AG9 VL domain.

SEQ ID NOs: 13 and 14 are the nucleotide and amino acid sequences of the 2BA2 VH domain.

SEQ ID NOs: 15 and 16 are the nucleotide and amino acid sequences of the 2BA2 VL domain.

SEQ ID NOs: 17 and 18 are the nucleotide and amino acid sequences of the 2BB5 VH domain.

SEQ ID NOs: 19 and 20 are the nucleotide and amino acid sequences of the 2BB5 VL domain.

SEQ ID NOs: 21 and 22 are the nucleotide and amino acid sequences of the 2BB6 VH domain.

SEQ ID NOs: 23 and 24 are the nucleotide and amino acid sequences of the 2BB6 VL domain.

SEQ ID NOs: 25 and 26 are the nucleotide and amino acid sequences of the 2BB7 VH domain.

SEQ ID NOs: 27 and 28 are the nucleotide and amino acid sequences of the 2BB7 VL domain.

SEQ ID NOs: 29 and 30 are the nucleotide and amino acid sequences of the 2BB8 VH domain.

SEQ ID NOs: 31 and 32 are the nucleotide and amino acid sequences of the 2BB8 VL domain.

SEQ ID NOs: 33 and 34 are the nucleotide and amino acid sequences of the 2BB10 VL domain.

DETAILED DESCRIPTION

I. Abbreviations

DPI days post infection
ELISA enzyme-linked immunosorbent assay
FITC fluorescein isothiocyanate
hMAb human monoclonal antibody
HRTV Heartland virus
IFA immunofluorescence assay
IP intraperitoneal
$LD_{50}$ lethal dose 50
LFA lateral flow assay
MAb monoclonal antibody
ME β-mercaptoethanol
MFI median fluorescent intensity
MHC major histocompatibility complex
MIA microsphere immunoassay
OD optical density
PE phycoerythrin
PFU plaque forming units
PRNT plaque reduction neutralization test
ROC receiver operator characteristic
RVFV Rift Valley fever virus
SFTSV severe fever with thrombocytopenia virus
TOSV Toscana virus II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The amino acid sequence boundaries of a given CDR can be readily determined using any of a number of well-known schemes, including those described by Kabat et al. (*Sequences of*

*Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., *JMB* 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are often identified by the chain in which the particular CDR is located. Thus, a $V_H$ CDR3 (or HCDR3) is located in the variable domain of the heavy chain of the antibody in which it is found, whereas a $V_L$ CDR1 (or LCDR1) is the CDR1 from the variable domain of the light chain of the antibody in which it is found. An antibody that binds HRTV N protein, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody.

A "humanized" immunoglobulin is an immunoglobulin including a human framework region and one or more complementarity determining regions (CDRs) from a non-human (for example a mouse, rat, or synthetic) immunoglobulin. The non-human immunoglobulin providing the CDRs is termed a "donor," and the human immunoglobulin providing the framework is termed an "acceptor." Generally, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Antigen: A compound, composition, or substance that can stimulate the production of antibodies or a T-cell response in an animal, including compositions that are injected or absorbed into an animal. An antigen reacts with the products of specific humoral or cellular immunity.

Antigen-specific: As used herein, an "antigen-specific" antibody is an antibody that was elicited (produced and/or activated) in response to a particular antigen. An "antigen-specific" antibody is capable of binding to the antigen, typically with high affinity.

Biological sample: A sample obtained from a subject (such as a human or veterinary subject). Biological samples, include, for example, fluid, cell and/or tissue samples. In some embodiments herein, the biological sample is a fluid sample. Fluid sample include, but are not limited to, serum, blood, plasma, urine, feces, saliva, cerebral spinal fluid (CSF) and bronchoalveolar lavage (BAL) fluid.

Complementarity determining region (CDR): Amino acid sequences which together define the binding affinity and specificity of the natural Fv region of a native Ig binding site. The light and heavy chains of an Ig each have three CDRs, designated LCDR1, LCDR2, LCDR3 and HCDR1, HCDR2 and HCDR3, respectively.

Conjugated: Refers to two molecules that are bonded together, for example by covalent bonds.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

Control: A reference standard, for example a positive control or negative control. A positive control is known to provide a positive test result. A negative control is known to provide a negative test result. However, the reference standard can be a theoretical or computed result, for example a result obtained in a population.

Detectable label: A detectable compound or composition that is conjugated directly or indirectly to another molecule, such as an antibody, protein or microparticle, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Diagnostic: Identifying the presence or nature of a pathologic condition, such as a viral infection. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis.

Epitope: An antigenic determinant Epitopes are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Fluorophore: A chemical compound, which when excited by exposure to a particular wavelength of light, emits light (i.e., fluoresces), for example at a different wavelength.

Examples of fluorophores that may be used in the compositions and methods disclosed herein are provided in U.S. Pat. No. 5,866,366 to Nazarenko et al.: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; R-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999).

Other suitable fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art may also be used.

Framework region: Amino acid sequences of an antibody that are interposed between CDRs. Framework regions include variable light and variable heavy framework regions. The framework regions serve to hold the CDRs in an appropriate orientation for antigen binding.

Fusion protein: A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Heartland virus (HRTV): A member of the *Phlebovirus* genus in the family Bunyaviridae. HRTV has a single-stranded RNA genome consisting of three genome segments—small (S), medium (M) and large (L). The nucleocapsid (N) protein of HRTV is encoded by the S segment. For other phleboviruses, the N protein has been shown to be immunodominant viral protein. HRTV was first isolated from two Missouri farmers in 2009 (McMullan et al., *N Engl J Med* 367: 834-841, 2012; PCT Publication No. 2013/142808). Infection with HRTV is characterized by symptoms of fever, headache, anorexia, gastrointestinal distress and fatigue. HRTV is transmitted by ticks.

Heterologous: A heterologous protein or polypeptide refers to a protein or polypeptide derived from a different source or species.

Hybridoma: A cell line or culture that secretes a homogenous population of monoclonal antibodies. Hybridomas are hybrid cells resulting from the fusion of a myeloma (tumor cell), which confers immortality, and an antibody-producing cell, which confers antibody specificity onto the hybridoma.

Immune complex: A protein complex that comprises an antibody bound to an antigen. In the context of the present disclosure, the term "immune complex" is used to indicate a protein complex that includes an antigen bound to two separate antigen-specific antibodies (each binding a different epitope of the antigen), whereas the term "antibody-antigen complex" is used to refer to an antigen bound to one antibody. Furthermore, the term "antibody-antibody complex" is used to refer to an antibody bound to a different antibody (such as an antigen-specific antibody bound to a secondary antibody). The term "microsphere immune complex" is used to indicate an immune complex conjugated to a microsphere.

Immunoconjugate: A covalent linkage of an effector molecule to an antibody or functional fragment thereof. The effector molecule can be, for example, a detectable label or an immunotoxin. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules."

Isolated: An "isolated" biological component (such as a nucleic acid, protein, antibody, antigen or virus) has been substantially separated or purified away from other biological components (such as cell debris, or other proteins or nucleic acids). Biological components that have been "isolated" include those components purified by standard purification methods. The term also embraces recombinant nucleic acids, proteins or viruses, as well as chemically synthesized nucleic acids or peptides.

Microparticle/microsphere: A particle that is generally about 0.01 to about 1000 microns in diameter. Microparticles include microspheres (spherical microparticles), beads, or the like with a surface suitable for binding (e.g., suitable for binding an antibody). For example, a microparticle can be a microsphere with a carboxylated surface. In some embodiments, the microparticles are polymeric microparticles (a microparticle made up of repeating subunits of a particular substance or substances). In some examples, the polymeric microparticles are polystyrene microparticles, such as a polystyrene microparticle with a carboxylated surface. Microspheres or beads for use in flow cytometry and flow instrumentation are well known in the art and are commercially available from a variety of sources.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies and conjugates disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in viral load. "Ameliorating" refers to the reduction in the number or severity of signs or symptoms of a disease, such as an infectious disease.

Phlebovirus: One of five genera of the Bunyaviridae family Phleboviruses are enveloped spherical viruses with icosahedral symmetry. The genome of phleboviruses consists of three single-stranded RNA genome segments—small (S), medium (M) and large (L). The M and L segments are negative sense RNA strands, while the S segment is ambisense RNA. The S segment encodes the non-structural protein NSs in the positive sense orientation and the nucleocapsid (N) in the negative sense orientation. The M segment encodes the glycoprotein precursor that is cleaved by host proteases into two structural domains—Gn and Gc. The L segment encodes the L protein, which functions as the RNA dependent RNA polymerase in primary and secondary transcription to generate mRNA and replicative intermediates, respectively. Phleboviruses have a worldwide distribution and are transmitted by a wide variety of arthropods, including sandflies, mosquitoes and ticks. Several phleboviruses have been linked to human disease, in some cases causing febrile illness, fever, hepatitis, meningitis, encephalitis or hemorrhagic syndrome.

Secondary antibody: An antibody that specifically recognizes the Fc region of a particular isotype of antibody (for example specifically recognizes human IgG or human IgM). Secondary antibodies for use with the methods disclosed herein include, but are not limited to, anti-human IgG and anti-human IgM. In some embodiments herein, the secondary antibody is conjugated to a detectable label, such as a fluorophore, enzyme or radioisotope, to facilitate detection of immune complexes to which the secondary antibody is bound.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds the HRTV N protein or a fragment thereof are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Serum: The fluid portion of the blood that separates out from clotted blood. Serum contains many proteins, including antibodies, but does not contain clotting factors.

Subject: Living multi-cellular vertebrate organisms, a category that includes both human and non-human mammals.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Heartland virus was first isolated from human leucocytes after two unrelated Missouri farmers were hospitalized in 2009. Next-generation sequencing and phylogenetic analysis confirmed the discovery of isolates of a novel bunyavirus of the genus *Phlebovirus*, which was subsequently named Heartland virus (HRTV). A subsequent field investigation resulted in the isolation of HRTV from *Amblyomma americanum* ticks. Therefore, a need surfaced for rapid and reliable serological assays to identify infection in patients.

In order to expand the diagnostic capabilities for detection of HRTV infection, twenty hybridoma clones secreting anti-HRTV murine monoclonal antibodies (MAbs) were developed using splenocytes from HRTV infected-AG129 receptor-interferon deficient mice. Nine of these MAbs were characterized for inclusion in HRTV diagnostic assays. All of the MAbs developed were found to be non-neutralizing and reactive to linear epitopes on HRTV nucleocapsid (N) protein. MAb 2AF11 was found to be cross-reactive with SFTSV.

In addition, microsphere assays were developed as a means of serological detection of both IgM and IgG antibodies in patient sera. HRTV antigens were captured by monoclonal antibodies covalently bound to microspheres, thus allowing for non-purified antigen preparations to be used. Antibodies in human sera from previously confirmed HRTV positive and negative cases were reacted with the microsphere complexes and detected by anti-human IgM or IgG antibodies coupled to phycoerythrin. Reactions were quantified using a BioPlex instrument. Cutoffs were determined by receiver operator characteristic (ROC) analysis, and the sensitivities, specificities and accuracies of the IgM and IgG microsphere immunoassays (MIA) were all >97% as determined by a bootstrap method. Within-plate precision ranged from 12-15% and between-plate precisions ranged from 7-18%. No cross-reactivity with other arboviruses was observed.

IV. Overview of Several Embodiments

Disclosed herein are monoclonal antibodies that specifically bind the N protein of HRTV. The HRTV N protein-specific monoclonal antibodies can be used in immunoassays to detect HRTV-specific antibodies in a biological sample or to detect HRTV in a cell or tissue sample. The monoclonal antibodies can also be used, for example, to diagnose or treat an HRTV infection.

The nucleotide and amino acid sequences of the variable heavy (VH) and variable light (VL) domains of the disclosed antibodies are provided below. In the amino acid sequences, the CDR sequences as determined by IMGT are underlined and the CDR sequences as determined by Kabat are shown in bold. The nucleotide positions and amino acid residues of the VL and VH domain CDRs are provided below each sequence. One of skill in the art could readily determine the CDR boundaries using alternative numbering schemes, such as the Chothia numbering scheme.

2AF11 VH DNA sequence (SEQ ID NO: 1)
CAGGTTACTCTGAAAGAGTCTGGCCCTGGGATATTGCAGCCCTCCCAGAC

CCTCAGTCTGACTTGTTCTTTCTCTGGGTTTTCACTGAGCACTTCTGGTA

TGAGTGTAGGCTGGATTCGTCAGCCTTCAGGGAAGGGTCTGGAGTGGCTG

GCACACATTTGGTGGAATGATGATATGTACTATAACCCAGCCCTGGAAAG

CCGGCTCACAATCTCCAAGGATACCTCCAACAACCAGGTTTTCCTCAAGA

-continued
TCGCCAGTGTGGTCACTGCAGATACTGCCACATACTACTGTGCTCGAATA

GCCCTAACTGGGCCCTACTGGTACTTCGATGTCTGGGGCGCAGGGACCAC

GGTCACCGTCTCCTCAGCCAAAACAACAGCCCCATCGGTCTATCCACTGG

CCCCTGTGTGTGGAGATACAACTGGCTCCTCGGTGACTCTAGGATGCCTG

GTCAAGGCTAGCATCCGAAT

2AF11 VH amino acid sequence
(SEQ ID NO: 2)
QVTLKESGPGILQPSQTLSLTCSFS<u>GFSLSTSGMSVG</u>WIRQPSGKGLEWL A<u>HIWWNDDMYYNPALESRL</u>TISKDTSNNQVFLKIASVVTADTATYYC<u>ARI</u>

<u>ALTGPYWYFDV</u>WGAGTTVTVSSAKTTAPSVYPLAPVCGDTTGSSVTLGCL

VK

| Locations of CDRs in 2AF11 VH sequence (according to Kabat) | | |
|---|---|---|
| CDR | DNA Sequence | Protein Sequence |
| CDR1 | Nucleotides 91-111 | Amino acids 31-37 |
| CDR2 | Nucleotides 154-201 | Amino acids 52-67 |
| CDR3 | Nucleotides 298-333 | Amino acids 100-111 |

| Locations of CDRs in 2AF11 VH sequence (according to IMGT) | | |
|---|---|---|
| CDR | DNA Sequence | Protein Sequence |
| CDR1 | Nucleotides 76-105 | Amino acids 26-35 |
| CDR2 | Nucleotides 157-177 | Amino acids 53-59 |
| CDR3 | Nucleotides 292-333 | Amino acids 98-111 |

2AF11 VL DNA sequence
(SEQ ID NO: 3)
GACATTGTGATGACCCAGACTCCAGCCTCCCTATCTGCATCTGTGGGAGA

AACTGTCACCATCACATGTCGAGCAAGTGAGAATATTTACAGTTATTTAG

CATGGTATCAGCAGAAACAGGGAAAATCTCCTCAGCTCCTGGTCAATAAT

GCAAAAACCTTAGCAGAAGGTGTGCCATCAAGGTTCAGTGGCAGTGGTTC

AGGCACACAGTTTTCTCTGAAGATCAACAGCCTGCAGCCTGAAGATTGTG

GGAATTATTACTGTCAACATCATTATGGCACTCCGCTCACGTTCGGTGCT

GGGACCAAGCTGGAGCTGAAA

2AF11 VL amino acid sequence
(SEQ ID NO: 4)
DIVMTQTPASLSASVGETVTITC<u>RAS<b>ENIYSYL</b>A</u>WYQQKGKSPQLLVN<u>N</u>

<u>AKTLAE</u>GVPSRFSGSGSGTQFSLKINSLQPEDCGNYYC<u><b>QHHYGTPLT</b></u>FGA

GTKLELK

| Locations of CDRs in 2AF11 VL sequence (according to Kabat) | | |
|---|---|---|
| CDR | DNA Sequence | Protein Sequence |
| CDR1 | Nucleotides 70-102 | Amino acids 24-34 |
| CDR2 | Nucleotides 148-168 | Amino acids 50-56 |
| CDR3 | Nucleotides 265-291 | Amino acids 89-97 |

| Locations of CDRs in 2AF11 VL sequence (according to IMGT) | | |
|---|---|---|
| CDR | DNA Sequence | Protein Sequence |
| CDR1 | Nucleotides 79-96 | Amino acids 27-32 |
| CDR2 | Nucleotides 148-156 | Amino acids 50-52 |
| CDR3 | Nucleotides 265-291 | Amino acids 89-97 |

2AG8 VH DNA sequence
(SEQ ID NO: 5)
GAAGTGCAGCTGGAGGAGTCTGGGGCTGAACTGGTGAGGTCTGGGGCCTC

ACTGAAGATGTCCTGCAAGGCTTCTGGCTACACATTTACCAGTTACAATC

TGCACTGGGTTAAGCAGACACCAGGACAGGGCCTGGAATGGATTGGATAT

ATTTTTCCTGGAAATGGTGGTACTGCCTACAATGAGAAGTTCAAGGGCAA

GGCCACATTGACTGCAGACACATCCTCCTCCACAGCCTACATGCAGATCA

GCAGCCTGACATCTGAGGACTCTGCGGTCTATTTCTGTGCAAGAGGGGGC

CCTTACTATGCTTTGGACTACTGGGGTCAAGGAACCTCAGTCACCGTCTC

CTCA

2AG8 VH amino acid sequence
(SEQ ID NO: 6)
VKLEESGAELVRSGASLKMSCKAS<u>GYTFTSYN</u>LHWVKQTPGQGLEWIGY<u>I</u>

<u>FPGNGGT</u>AYNEKFKGKATLTADTSSSTAYMQISSLTSEDSAVYFC<u>ARGGP</u>

<u>YYALDY</u>WGQGTSVTVSS

| Locations of CDRs in 2AG8 VH sequence (according to Kabat) | | |
|---|---|---|
| CDR | DNA Sequence | Protein Sequence |
| CDR1 | Nucleotides 92-105 | Amino acids 30-34 |
| CDR2 | Nucleotides 148-198 | Amino acids 49-65 |
| CDR3 | Nucleotides 295-321 | Amino acids 98-106 |

| Locations of CDRs in 2AG8 VH sequence (according to IMGT) | | |
|---|---|---|
| CDR | DNA Sequence | Protein Sequence |
| CDR1 | Nucleotides 76-99 | Amino acids 25-33 |
| CDR2 | Nucleotides 151-174 | Amino acids 50-57 |
| CDR3 | Nucleotides 289-321 | Amino acids 96-106 |

2AG8 VL DNA sequence
(SEQ ID NO: 7)
GACATTGTGATGACCCAGTCTCCAGCCTCCCTATCTGCATCTGTGGGAGA

AACTGTCACCATCACATGTCGAACAAGTGGGAATATTCACACTTATTTAG

CATGGTATCAGCACAAACAGGGAAAATCTCCTCAGCTCCTGGTCTATTAT

GCAAAAACCTTAGCAGATGGTGTGCCATCAAGGTTCAGTGGCAGTGGATC

AGGAACACAATATTCTCTCAAGATCAACAGCCTGCAGCCTGAAGATTTTG

GGAGTTATTACTGTCAACATTTTGGAGTAATCCTCGGACGTTCGGTGGA

GGCACCAAGCTGGAAATCAAA

2AG8 VL amino acid sequence
(SEQ ID NO: 8)
DIVMTQSPASLSASVGETVTITC<u>RTS<b>GNIHTYL</b>A</u>WYQHKGKSPQLLVY<u><b>Y</b></u>

-continued

AKTLADGVPSRFSGSGSGTQYSLKINSLQPEDFGSYYCQHFWSNPRTFGG

GTKLEIKRADAAPTVS

| Locations of CDRs in 2AG8 VL sequence (according to Kabat) | | |
|---|---|---|
| CDR | DNA Sequence | Protein Sequence |
| CDR1 | Nucleotides 70-102 | Amino acids 24-34 |
| CDR2 | Nucleotides 148-168 | Amino acids 50-56 |
| CDR3 | Nucleotides 265-291 | Amino acids 89-97 |

| Locations of CDRs in 2AG8 VL sequence (according to IMGT) | | |
|---|---|---|
| CDR | DNA Sequence | Protein Sequence |
| CDR1 | Nucleotides 79-96 | Amino acids 27-32 |
| CDR2 | Nucleotides 148-156 | Amino acids 50-52 |
| CDR3 | Nucleotides 265-291 | Amino acids 89-97 |

2AG9 VH DNA sequence
(SEQ ID NO: 9)
GAACTGGCAAGACCTGGGGCTTCAGTGAAGTTGTCCTGCAAGGCTTCTGG

CTACACCTTTACTAATTACTATATGCAGTGGATAAAACAGCGGCCTGGAC

AGGGTCTGGAGTGGATTGGGCTGTTTATCCTGGAGATGGTGATACTAGG

TACACTCAGAAGTTCAAGGGCAAGGCCTCATTGACTGCAGATAAATCCTC

CACCACAGCCTATATGCAACTCAGCAGCTTGGCATCTGAGGACTCTGCGG

TCTATTACTGTACAAGGGGAGATTACGAGGGAACCTGGTTTACTTACTGG

GGCCAAGGGACTCTGGTCACTGTCTCTGCA

2AG9 VH amino acid sequence
(SEQ ID NO: 10)
ELARPGASVKLSCKASGYTFTNYYMQWIKQRPGQGLEWIGAVYPGDGDTR

YTQKFKGKASLTADKSSTTAYMQLSSLASEDSAVYYCTRGDYEGTWFTYW

GQGTLVTVSA

| Locations of CDRs in 2AG9 VH sequence (according to Kabat) | | |
|---|---|---|
| CDR | DNA Sequence | Protein Sequence |
| CDR1 | Nucleotides 64-78 | Amino acids 22-26 |
| CDR2 | Nucleotides 121-171 | Amino acids 41-57 |
| CDR3 | Nucleotides 268-297 | Amino acids 90-99 |

| Locations of CDRs in 2AG9 VH sequence (according to IMGT) | | |
|---|---|---|
| CDR | DNA Sequence | Protein Sequence |
| CDR1 | Nucleotides 49-72 | Amino acids 17-24 |
| CDR2 | Nucleotides 124-147 | Amino acids 42-49 |
| CDR3 | Nucleotides 262-297 | Amino acids 88-99 |

2AG9 VL DNA sequence
(SEQ ID NO: 11)
GATATTGTGATGACCCAGACTCCAGCAATCATGTCTGCATCTCCAGGGGA

GAAGGTCACCATGACCTGCAGTGCCAGCTCAAGTGTAAGTTACATGCACT

GGTACCAGCAGAAGTCAGGCACCTCCCCCAAAAGATGGATGTATGACACA

TCCAAACTGGCTTCTGGAGTCCCTGGTCGCTTCAGTGGCAGTGGGTCTGG

GACCACTTACTCTCTCACAATCAGCACCATGGAGGCTGAAGATGCTGCCA

CCTATTACTGCCAGCAGTGGAGTAGTAACCCACCCACGTTCGGGGGGGGG

ACCAAGCTGGAAATAAAA

2AG9 VL amino acid sequence
(SEQ ID NO: 12)
DIVMTQTTAIMSASPGEKVTMTCSASSSVSYMHWYQQKSGTSPKRWMYDT

SKLASGVPGRFSGSGSGTTYSLTISTMEAEDAATYYCQQWSSNPPTFGGG

TKLEIK

| Locations of CDRs in 2AG9 VL sequence (according to Kabat) | | |
|---|---|---|
| CDR | DNA Sequence | Protein Sequence |
| CDR1 | Nucleotides 70-99 | Amino acids 24-33 |
| CDR2 | Nucleotides 145-165 | Amino acids 49-55 |
| CDR3 | Nucleotides 262-288 | Amino acids 88-96 |

| Locations of CDRs in 2AG9 VL sequence (according to IMGT) | | |
|---|---|---|
| CDR | DNA Sequence | Protein Sequence |
| CDR1 | Nucleotides 79-93 | Amino acids 27-31 |
| CDR2 | Nucleotides 145-153 | Amino acids 49-51 |
| CDR3 | Nucleotides 262-288 | Amino acids 88-96 |

2BA2 VH DNA sequence
(SEQ ID NO: 13)
GTGCAGCTGCAGGAGTCGGGACCTGGCCTCGTGAAACCTTCGCAGCCTCT

GTCTCTCACCTGCTCTGTCACTGGCTACTCCATTACCAGTGCTTATTACT

GGAACTGGATCCGGCAGTTTCCAGGAAACAAACTGGAATGGATGGGATAC

ATAACCTACGACGGTACCAATAACTACAACCCATCTCTCAAAAATCGAAT

CTCCATCACTCGTGACACATCTAAGAACCAGTTTTTCCTGAAGTTGAATT

CTGTGACTACTGAGGACACAGCTTCATATTACTGTGCAAGAGATGTTGCT

ACGGTCGGTGCTATGGACTACTGGGGTCAAGGAACCTCAGTCACCGTCTC

CTCA

2BA2 VH amino acid sequence
(SEQ ID NO: 14)
VQLQESGPGLVKPSQPLSLTCSVTGYSITSAYYWNWIRQFPGNKLEWMGY

ITYDGTNNYNPSLKNRISITRDTSKNQFFLKLNSVTTEDTASYYCARDVA

TVGAMDYWGQGTSVTVSS

Locations of CDRs in 2BA2 VH sequence (according to Kabat)

| CDR | DNA Sequence | Protein Sequence |
| --- | --- | --- |
| CDR1 | Nucleotides 88-105 | Amino acids 30-35 |
| CDR2 | Nucleotides 148-195 | Amino acids 50-65 |
| CDR3 | Nucleotides 292-321 | Amino acids 98-107 |

Locations of CDRs in 2BA2 VH sequence (according to IMGT)

| CDR | DNA Sequence | Protein Sequence |
| --- | --- | --- |
| CDR1 | Nucleotides 73-99 | Amino acids 25-33 |
| CDR2 | Nucleotides 151-171 | Amino acids 51-57 |
| CDR3 | Nucleotides 286-321 | Amino acids 96-107 |

2BA2 VL DNA sequence
(SEQ ID NO: 15)
AGTATTGTGATGACCCAGACTCCCAAATTCCTGCTTGTATCAGCAGGAGA

CAGGGTTACCATAACCTGCAAGGCCAGTCAGAGTGTGAGTAATGATGTAG

CTTGGTACCAACAGAAGCCAGGGCAGTCTCCTAAACTGCTGATATACTTT

GCATCCAATCGCTACACTGGAGTCCCTGATCGCTTCACTGGCAGTGGATA

TGGGACGGATTTCACTTTCACCATCAGCACTGTGCTGGCTGAAGACCTGG

CACTTTATTTCTGTCAGCAGGATTATAGCTCTCCTCGGACGTTCGGTGGA

GGCACCAAACTGGAAGTCAAA

2BA2 VL amino acid sequence
(SEQ ID NO: 16)
SIVMTQTPKFLLVSAGDRVTITCKASQSVSNDVAWYQQKPGQSPKLLIY**F
ASNRYTGVPDRFTGSGYGTDFTFTISTVLAEDLALYFCQQDYSSPRT**FGG

GTKLEVK

Locations of CDRs in 2BA2 VL sequence (according to Kabat)

| CDR | DNA Sequence | Protein Sequence |
| --- | --- | --- |
| CDR1 | Nucleotides 70-102 | Amino acids 24-34 |
| CDR2 | Nucleotides 148-168 | Amino acids 50-56 |
| CDR3 | Nucleotides 265-291 | Amino acids 89-97 |

Locations of CDRs in 2BA2 VL sequence (according to IMGT)

| CDR | DNA Sequence | Protein Sequence |
| --- | --- | --- |
| CDR1 | Nucleotides 79-96 | Amino acids 27-32 |
| CDR2 | Nucleotides 148-156 | Amino acids 50-53 |
| CDR3 | Nucleotides 265-291 | Amino acids 89-97 |

2BB5 VH DNA sequence
(SEQ ID NO: 17)
GAGGTGCAGCTGGAGGAGTCAGGAGGAGGCTTGGTGCAACCTGGAGGATC

CATGAAACTCTCCTGTGTTGCCTCTGGATTCACTTTCAGTAACTACTGGA

TGAACTGGGTCCGCCAGTCTCCAGAGAAGGGGCTTGAGTGGGTTGCTGAA

GTTAGATTGAATTCTAATAATTATGCAACACATTATGCGGAGTCTGTGAA

AGGGAGGTTCACCATCTCAAGAGATGATTCCAAAAGTAGTGTCTACCTGC

AAATGAGCAACTTAAGATCTGAAGACACTGGCATTTATTATTGTTCCACC

GATTATTACGGCTATGCTATGGACTACTGGGGTCAAGGAACCCTCAGTCAC

CGTCTCCTCA

2BB5 VH amino acid sequence
(SEQ ID NO: 18)
EVQLEESGGGLVQPGGSMKLSCVASGFTFSNYWMNWVRQSPEKGLEWVAE
VRLNSNNYATHYAESVKGRFTISRDDSKSSVYLQMSNLRSEDTGIYYCST
DYYGYAMDYWGQGTSVTVSS Locations of CDRs in 2BB5 VH sequence (according to Kabat)

| CDR | DNA Sequence | Protein Sequence |
| --- | --- | --- |
| CDR1 | Nucleotides 91-105 | Amino acids 31-35 |
| CDR2 | Nucleotides 148-204 | Amino acids 50-68 |
| CDR3 | Nucleotides 301-327 | Amino acids 101-109 |

Locations of CDRs in 2BB5 VH sequence (according to IMGT)

| CDR | DNA Sequence | Protein Sequence |
| --- | --- | --- |
| CDR1 | Nucleotides 79-99 | Amino acids 26-33 |
| CDR2 | Nucleotides 151-180 | Amino acids 51-60 |
| CDR3 | Nucleotides 295-327 | Amino acids 99-109 |

2BB5 VL DNA sequence
(SEQ ID NO: 19)
GATATTGTGATGACCCAGACTCCATCAATCATGTCTGCATCTCCAGGGGA

GAAGGTCACCATAACCTGCAGTGCCAGCTCTAATGTAAATTACATGCACT

GGTTCCAGCAGAAGCCAGGCACTTCTCCCAAACTCTGGATTTATAGCACA

TCCAACCTGGCTTCTGGAGTCCCTGCTCGCTTCAGTGGCAGTGGATCTGG

GACCTCTTACTCTCTCACAATCAGCCGAATGGAGGCTGAAGATGCTGCCA

CTTATTACTGCCAGCAAAGGAGTAATTACCCACCCACGTTCGGTGCTGGG

ACCAAGCTGGAGCTGAAA

2BB5 VL amino acid sequence
(SEQ ID NO: 20)
DIVMTQTPSIMSASPGEKVTITCSASSNVNYMHWFQQKPGTSPKLWIY**ST
SNLASGVPARFSGSGSGTSYSLTISRMEAEDAATYYCQQRSNYPPT**FGAG

TKLELK

Locations of CDRs in 2BB5 VL sequence (according to Kabat)

| CDR | DNA Sequence | Protein Sequence |
| --- | --- | --- |
| CDR1 | Nucleotides 70-99 | Amino acids 24-33 |
| CDR2 | Nucleotides 145-165 | Amino acids 49-55 |
| CDR3 | Nucleotides 262-288 | Amino acids 88-96 |

| Locations of CDRs in 2BB5 VL sequence (according to IMGT) | | |
|---|---|---|
| CDR | DNA Sequence | Protein Sequence |
| CDR1 | Nucleotides 79-93 | Amino acids 27-31 |
| CDR2 | Nucleotides 145-153 | Amino acids 49-51 |
| CDR3 | Nucleotides 262-288 | Amino acids 88-96 |

2BB6 VH DNA sequence
(SEQ ID NO: 21)
GAGGTTCAGCTGGAGGAGTCAGGACCTGACCTGGTGAAACCTTCTCAGTC

ACTTTCACTCACCTGCACTGTCACTGGCTTCTCCATCACCAGTGGTTATA

GTTGGCACTGGATCCGGCAATTTCCAGGAAACAAACTGGAATGGATGGGC

TACATACACTTCAGTGGTAGCACGAACTACAACCCATCTCTCAAAAGTCG

AATCTCTATCACTCGAGACACATCCAAGAACCAGTTCTTCCTGCAGTTGA

GTTCTGTGACTACTGACGACAGGCACATATTACTGTGCAAGAGATCTG

ACTGGGATTGACTCCTGGGGCCAAGGCACCACTCTCACAGTCTCCTCA

2BB6 VH amino acid sequence
(SEQ ID NO: 22)
EVQLEESGPDLVKPSQSLSLTCTVTGFSITSGYSWHWIRQFPGNKLEWMG

YIHFSGSTNYNPSLKSRISITRDTSKNQFFLQLSSVTTDDTGTYYCARDL

TGIDSWGQGTTLTVSS

| Locations of CDRs in 2BB6 VH sequence (according to Kabat) | | |
|---|---|---|
| CDR | DNA Sequence | Protein Sequence |
| CDR1 | Nucleotides 91-108 | Amino acids 31-36 |
| CDR2 | Nucleotides 151-198 | Amino acids 51-66 |
| CDR3 | Nucleotides 295-315 | Amino acids 99-105 |

| Locations of CDRs in 2BB6 VH sequence (according to IMGT) | | |
|---|---|---|
| CDR | DNA Sequence | Protein Sequence |
| CDR1 | Nucleotides 76-102 | Amino acids 26-34 |
| CDR2 | Nucleotides 154-174 | Amino acids 52-58 |
| CDR3 | Nucleotides 289-315 | Amino acids 97-105 |

2BB6 VL DNA sequence
(SEQ ID NO: 23)
GATATTGTGATGACACAGACTCCAGCAATCATGTCTGCATCTCCAGGGGA

GAAGGTCACCATATCCTGCAGTGCCAGCTCAAGTGTAAGTTACATGTACT

GGTTCCAGCAGAAGCCAGGATCCTCCCCCAAACCCTGGATTTATCGCACA

TCCAACCTGGCTTCTGGAGTCCCTGCTCGCTTCAGTGGCAGTGGGTCTGG

GACCTCTTACTCTGTCACAATCAGCAGCATGGAGGCTGAAGATGCTGCCA

CTTATTACTGCCAGCAGTATCATAGTTACCCACTCACGTTCGGTGCTGGG

ACCAAGCTGGAGCTGAAA

2BB6 VL amino acid sequence
(SEQ ID NO: 24)
DIVMTQTPAIMSASPGEKVTISCSASSSVSYMYWFQQKPGSSPKPWIYRT

SNLASGVPARFSGSGSGTSYSVTISSMEAEDAATYYCQQYHSYPLTFGAG

TKLELK

| Locations of CDRs in 2BB6 VL sequence (according to Kabat) | | |
|---|---|---|
| CDR | DNA Sequence | Protein Sequence |
| CDR1 | Nucleotides 70-99 | Amino acids 24-33 |
| CDR2 | Nucleotides 145-165 | Amino acids 49-55 |
| CDR3 | Nucleotides 262-288 | Amino acids 88-96 |

| Locations of CDRs in 2BB5 VL sequence (according to IMGT) | | |
|---|---|---|
| CDR | DNA Sequence | Protein Sequence |
| CDR1 | Nucleotides 79-93 | Amino acids 27-31 |
| CDR2 | Nucleotides 145-153 | Amino acids 49-51 |
| CDR3 | Nucleotides 262-288 | Amino acids 88-96 |

2BB7 VH DNA sequence
(SEQ ID NO: 25)
GAGGTCCAGCTGCAACAGTCTGGACCTGACCTGGTGAAGCCTGGAGCTTC

AATGAAGATATCCTGCAAGGCTTCTGGTTACTCATTCACTGCCTACACCA

TGAACTGGGTGAAGCAGAGCCATGGAAAGAACCTTGAGTGGATTGGACTT

ATTAGTCCTTACAATGGTGGTACTAGTTACAACCAGAAGTTCAAGGGCAA

GGCCACATTAACTGTAGACAAGTCATCCAGCACAGCCTACATGGAGCTCC

TCAGTCTGACATCTGAGGACTCTGCAGTCTATTACTGTGCAAGACAGATC

GGGCCTTACTTTGACCATTGGGGCCAAGGCACCACTCTCACAGTCTCCTC

A

2BB7 VH amino acid sequence
(SEQ ID NO: 26)
EVQLQQSGPDLVKPGASMKISCKASGYSFTAYTMNWVKQSHGKNLEWIGL

ISPYNGGTSYNQKFKGKATLTVDKSSSTAYMELLSLTSEDSAVYYCARQI

GPYFDHWGQGTTLTVSS

| Locations of CDRs in 2BB7 VH sequence (according to Kabat) | | |
|---|---|---|
| CDR | DNA Sequence | Protein Sequence |
| CDR1 | Nucleotides 91-105 | Amino acids 31-35 |
| CDR2 | Nucleotides 148-198 | Amino acids 50-66 |
| CDR3 | Nucleotides 295-318 | Amino acids 99-106 |

| Locations of CDRs in 2BB7 VH sequence (according to IMGT) | | |
|---|---|---|
| CDR | DNA Sequence | Protein Sequence |
| CDR1 | Nucleotides 76-99 | Amino acids 26-33 |
| CDR2 | Nucleotides 151-174 | Amino acids 51-58 |
| CDR3 | Nucleotides 289-318 | Amino acids 97-106 |

2BB7 VL DNA sequence
(SEQ ID NO: 27)
GACATTGTGATGACCCAGACTCCATCTTCCATGTATGCATCTCTAGGAGA

GAGAGTCACTATCACTTGCAAGGCGAGTCAGGACATTAAAAGCTCTTTTA

GTTGGTTCCAGCAGAAACCAGGGAAATCTCCTAAGACCCTGATCTATCGT

GCAAGCAGATTGGTAGATGGGGTCCCATCAAGGTTCAGTGGCAGTGGATC

TGGGCAAGATTCTTCTCTCACCATCAGCAGCCTGGAGTATGAAGATATGG

GAATTTATTATTGTCTACAGTGTGATGAGTTTCCGTACACGTTCGGAGGG

GGGACCAAGCTGGAAATAAAA

2BB7 VL amino acid sequence
(SEQ ID NO: 28)
DIVMTQTTPSSMYASLGERVTITCKASQDIKSSFSWFQQKPGKSPKTLIY

RASRLVDGVPSRFSGSGSGQDSSLTISSLEYEDMGIYYCLQCDEFPYTFG

GGTKLEIK

| Locations of CDRs in 2BB7 VL sequence (according to Kabat) | | |
|---|---|---|
| CDR | DNA Sequence | Protein Sequence |
| CDR1 | Nucleotides 70-102 | Amino acids 24-34 |
| CDR2 | Nucleotides 148-168 | Amino acids 50-56 |
| CDR3 | Nucleotides 265-291 | Amino acids 89-97 |

| Locations of CDRs in 2BB7 VL sequence (according to IMGT) | | |
|---|---|---|
| CDR | DNA Sequence | Protein Sequence |
| CDR1 | Nucleotides 79-96 | Amino acids 27-32 |
| CDR2 | Nucleotides 148-156 | Amino acids 50-52 |
| CDR3 | Nucleotides 265-291 | Amino acids 89-97 |

2BB8 VH DNA sequence
(SEQ ID NO: 29)
CAGGCTTATCTACAGCAGTCTGGGGCTGAACTGGTGAGGTCTGGGCCTC

ACTGAAGATGTCCTGCAAGGCTTCTGGCTACACATTTACCAGTTACAATC

TGCACTGGGTTAAGCAGACACCAGGACAGGGCCTGGAATGGATTGGATAT

ATTTTTCCTGGAAATGGTGGTACTGCCTACAATGAGAAGTTCAAGGGCAA

GGCCACATTGACTGCAGACACATCCTCCTCCACAGCCTACATGCAGATCA

GCAGCCTGACATCTGAGGACTCTGCGGTCTATTTCTGTGCAAGAGGGGGC

CCTTACTATGCTTTGGACTACTGGGGTCAAGGAACCTCAGTCACCGTCTC

CTCAG

2BB8 VH amino acid sequence
(SEQ ID NO: 30)
QAYLQQSGAELVRSGASLKMSCKASGYTFTSYNLHWVKQTPGQGLEWIGY

IFPGNGGTAYNEKFKGKATLTADTSSSTAYMQISSLTSEDSAVYFCARGG

PYYALDYWGQGTSVTVSS

| Locations of CDRs in 2BB8 VH sequence (according to Kabat) | | |
|---|---|---|
| CDR | DNA Sequence | Protein Sequence |
| CDR1 | Nucleotides 91-105 | Amino acids 31-35 |
| CDR2 | Nucleotides 148-198 | Amino acids 50-66 |
| CDR3 | Nucleotides 295-321 | Amino acids 99-107 |

| Locations of CDRs in 2BB8 VH sequence (according to IMGT) | | |
|---|---|---|
| CDR | DNA Sequence | Protein Sequence |
| CDR1 | Nucleotides 76-99 | Amino acids 26-33 |
| CDR2 | Nucleotides 151-174 | Amino acids 51-58 |
| CDR3 | Nucleotides 289-321 | Amino acids 97-107 |

2BB8 VL DNA sequence
(SEQ ID NO: 31)
GACATCCAGATGACTCAGTCTCCAGCCTCCCTATCTGCATCTGTGGGAGA

AACTGTCACCATCACATGTCGAACAAGTGGGAATATTCACACTTATTTAG

CATGGTATCAGCACAAACAGGGAAATCTCCTCAGCTCCTGGTCTATTAT

GCAAAAACCTTAGCAGATGGTGTGCCATCAAGGTTCAGTGGCAGTGGATC

AGGAACACAATATTCTCTCAAGATCAACAGCCTGCAGCCTGAAGATTTTG

GGAGTTATTACTGTCAACATTTTTGGAGTAATCCTCGGACGTTCGGTGGA

GGCACCAAGCTGGAAATCAAA

2BB8 VL amino acid sequence
(SEQ ID NO: 32)
DIQMTQSPASLSASVGETVTITCRTSGNIHTYLAWYQHKQGKSPQLLVYY

AKTLADGVPSRFSGSGSGTQYSLKINSLQPEDFGSYYCQHFWSNPRTFGG

GTKLEIK

| Locations of CDRs in 2BB8 VL sequence (according to Kabat) | | |
|---|---|---|
| CDR | DNA Sequence | Protein Sequence |
| CDR1 | Nucleotides 70-102 | Amino acids 24-34 |
| CDR2 | Nucleotides 148-168 | Amino acids 50-56 |
| CDR3 | Nucleotides 265-291 | Amino acids 89-97 |

| Locations of CDRs in 2BB8 VL sequence (according to IMGT) | | |
|---|---|---|
| CDR | DNA Sequence | Protein Sequence |
| CDR1 | Nucleotides 79-96 | Amino acids 27-32 |
| CDR2 | Nucleotides 148-156 | Amino acids 50-52 |
| CDR3 | Nucleotides 265-291 | Amino acids 89-97 |

2BB10 VL DNA sequence
(SEQ ID NO: 33)
GATATTGTGATGACACAGACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

-continued

```
CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

TGGACGTTCGGTGGAGGCACCAAGCTGGAAATCAAA

2BB10 VL amino acid sequence
                                          (SEQ ID NO: 34)
DIVMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

WTFGGGTKLEIK
```

| Locations of CDRs in 2BB10 VL sequence (according to Kabat) | | |
|---|---|---|
| CDR | DNA Sequence | Protein Sequence |
| CDR1 | Nucleotides 70-117 | Amino acids 24-39 |
| CDR2 | Nucleotides 163-183 | Amino acids 55-61 |
| CDR3 | Nucleotides 280-306 | Amino acids 94-102 |

| Locations of CDRs in 2BB10 VL sequence (according to IMGT) | | |
|---|---|---|
| CDR | DNA Sequence | Protein Sequence |
| CDR1 | Nucleotides 79-111 | Amino acids 27-37 |
| CDR2 | Nucleotides 163-171 | Amino acids 55-57 |
| CDR3 | Nucleotides 280-306 | Amino acids 94-102 |

Provided herein are isolated monoclonal antibodies specific for the N protein of HRTV, and antigen-binding fragments thereof. The monoclonal antibodies or antigen-binding fragments comprise a VH domain and/or a VL domain. In some embodiments, the VH domain of the antibody or antigen-binding fragment comprises at least a portion of the amino acid sequence set forth herein as any one of SEQ ID NOs: 2, 6, 10, 14, 18, 22, 26 and 30, such as one or more (such as all three) CDR sequences from any one of SEQ ID NOs: 2, 6, 10, 14, 18, 22, 26 and 30. In some embodiments, the VL domain of the antibody or antigen-binding fragment comprises at least a portion of the amino acid sequence set forth herein as any one of SEQ ID NOs: 4, 8, 12, 16, 20, 24, 28, 32 and 34, such as one or more (such as all three) CDR sequences from any one of SEQ ID NOs: 4, 8, 12, 16, 20, 24, 28, 32 and 34. In some examples, the CDR locations are determined IMGT, Kabat or Chothia.

In some embodiments, the VH domain CDR sequences are at least 90%, at least 91%, at least 92%, at least 93%, at least 94%, at least 95%, at least 96%, at least 97%, at least 98% or at least 99% identical to the CDR sequences of any one of SEQ ID NOs: 2, 6, 10, 14, 18, 22, 26 and 30 and/or the VL domain CDR sequences are at least 90%, at least 91%, at least 92%, at least 93%, at least 94%, at least 95%, at least 96%, at least 97%, at least 98% or at least 99% identical to the CDR sequences of any one of SEQ ID NOs: 4, 8, 12, 16, 20, 24, 28, 32 and 34.

In some embodiments of the monoclonal antibody or antigen-binding fragment, the VH domain comprises residues 26-35, 53-59 and 98-111 of SEQ ID NO: 2 and/or the VL domain comprises residues 27-32, 50-52 and 89-97 of SEQ ID NO: 4; the VH domain comprises residues 25-33, 50-57 and 96-106 of SEQ ID NO: 6 and/or the VL domain comprises residues 27-32, 50-52 and 89-97 of SEQ ID NO: 8; the VH domain comprises residues 17-24, 42-49 and 88-99 of SEQ ID NO: 10 and/or the VL domain comprises residues 27-31, 49-51 and 88-96 of SEQ ID NO: 12; the VH domain comprises residues 25-33, 51-57 and 96-107 of SEQ ID NO: 14 and/or the VL domain comprises residues 27-32, 50-53 and 89-97 of SEQ ID NO: 16; the VH domain comprises residues 26-33, 51-60 and 99-109 of SEQ ID NO: 18 and/or the VL domain comprises residues 27-31, 49-51 and 88-96 of SEQ ID NO: 20; the VH domain comprises residues 26-34, 52-58 and 97-105 of SEQ ID NO: 22 and/or the VL domain comprises residues 27-31, 49-51 and 88-96 of SEQ ID NO: 24; the VH domain comprises residues 26-33, 51-58 and 97-106 of SEQ ID NO: 26 and/or the VL domain comprises residues 27-32, 50-52 and 89-97 of SEQ ID NO: 28; or the VH domain comprises residues 26-33, 51-58 and 97-107 of SEQ ID NO: 30 and/or the VL domain comprises residues 27-32, 50-52 and 89-97 of SEQ ID NO: 32.

In some embodiments of the monoclonal antibody or antigen-binding fragment, the VH domain comprises residues 31-37, 52-67 and 100-111 of SEQ ID NO: 2 and/or the VL domain comprises residues 24-34, 50-56 and 89-97 of SEQ ID NO: 4; the VH domain comprises residues 30-34, 49-65 and 98-106 of SEQ ID NO: 6 and/or the VL domain comprises residues 24-34, 50-56 and 89-97 of SEQ ID NO: 8; the VH domain comprises residues 22-26, 41-57 and 90-99 of SEQ ID NO: 10 and/or the VL domain comprises residues 24-34, 49-55 and 88-96 of SEQ ID NO: 12; the VH domain comprises residues 30-35, 50-65 and 98-107 of SEQ ID NO: 14 and/or the VL domain comprises residues 24-34, 50-56 and 89-97 of SEQ ID NO: 16; the VH domain comprises residues 31-35, 50-68 and 101-109 of SEQ ID NO: 18 and/or the VL domain comprises residues 24-33, 49-55 and 88-96 of SEQ ID NO: 20; the VH domain comprises residues 31-36, 51-66 and 99-105 of SEQ ID NO: 22 and/or the VL domain comprises residues 24-33, 49-55 and 88-96 of SEQ ID NO: 24; the VH domain comprises residues 31-35, 50-66 and 99-106 of SEQ ID NO: 26 and/or the VL domain comprises residues 24-34, 50-56 and 89-97 of SEQ ID NO: 28; or the VH domain comprises residues 31-35, 50-66 and 99-107 of SEQ ID NO: 30 and/or the VL domain comprises residues 24-34, 50-56 and 89-97 of SEQ ID NO: 32.

In some embodiments, the VH domain comprises an amino acid sequence at least 80%, at least 85%, at least 90%, at least 95%, at least 96%, at least 97%, at least 98% or at least 99% identical to SEQ ID NO: 2, SEQ ID NO: 6, SEQ ID NO: 10, SEQ ID NO: 14, SEQ ID NO: 18, SEQ ID NO: 22, SEQ ID NO: 26 or SEQ ID NO: 30. In some examples, the VH domain comprises or consists of the amino acid sequence of SEQ ID NO: 2, SEQ ID NO: 6, SEQ ID NO: 10, SEQ ID NO: 14, SEQ ID NO: 18, SEQ ID NO: 22, SEQ ID NO: 26 or SEQ ID NO: 30.

In some embodiments, the VL domain comprises an amino acid sequence at least 80%, at least 85%, at least 90%, at least 95%, at least 96%, at least 97%, at least 98% or at least 99% identical to SEQ ID NO: 4, SEQ ID NO: 8, SEQ ID NO: 12, SEQ ID NO: 16, SEQ ID NO: 20, SEQ ID NO: 24, SEQ ID NO: 28 or SEQ ID NO: 32. In some examples, the VL domain comprises or consists of the amino acid sequence of SEQ ID NO: 4, SEQ ID NO: 8, SEQ ID NO: 12, SEQ ID NO: 16, SEQ ID NO: 20, SEQ ID NO: 24, SEQ ID NO: 28 or SEQ ID NO: 32.

In some embodiments, the monoclonal antibody is an immunoglobulin (Ig) molecule, such as an IgG antibody. In other embodiments, the monoclonal antibody is an IgA, IgD, IgE or IgM antibody.

In some embodiments, the antigen-binding fragment is an Fab fragment, an Fab' fragment, an F(ab)'$_2$ fragment, a single chain variable fragment (scFv) or a disulfide stabilized variable fragment (dsFv).

In some embodiments, the monoclonal antibody or antigen-binding fragment is a mouse antibody. In other embodiments, the monoclonal antibody or antigen-binding fragment is a chimeric or synthetic antibody comprising human and mouse amino acid sequence. For example, the antibody can comprise one or more human framework regions. In other embodiments, the monoclonal antibody or antigen-binding fragment is humanized.

Also provided herein are fusion proteins comprising a monoclonal antibody or antigen-binding fragment disclosed herein and a heterologous protein. In some examples, the heterologous protein is a protein tag, such as a myc tag, His tag, HA tag, or FLAG tag. In other examples, the heterologous protein is an affinity tag, such as chitin binding protein, maltose binding protein, or glutathione-S-transferase (GST).

Further provided herein are immunoconjugates comprising a monoclonal antibody or antigen-binding fragment disclosed herein attached to a detectable label. In some embodiments, the detectable label is a fluorescent, radioactive or enzymatic label.

Compositions comprising a monoclonal antibody or antigen-binding fragment disclosed herein and a pharmaceutically acceptable carrier are further provided.

Also provided are compositions that include a disclosed monoclonal antibody or antigen-binding fragment conjugated to a microsphere. Microspheres for use in immunoassays are well known in the art and are commercially available from a variety of sources. In some examples, the microspheres are MICROPLEX™ microspheres (Luminex Corp, Austin, Tex.). The antibody or antigen-binding fragment can be conjugated to the microsphere using any method known in the art. In some embodiments, the monoclonal antibody or antigen-binding fragment is chemically conjugated to the microsphere. In some examples, chemical conjugation is via carbodiimide coupling. In some embodiments, the microsphere comprises a fluorophore. In some examples, the microsphere comprises two different fluorophores.

In some embodiments, the antibody-microsphere compositions further include HRTV N protein bound to the monoclonal antibody or antigen-binding fragment (referred to herein as "microsphere compositions"). The source of the N protein can include, for example, recombinantly prepared N protein, lysates of cells expressing N protein or lysates of HRTV-infected cells.

Further provided herein are methods of detecting HRTV-specific antibodies in a biological sample. In some embodiments, the method is a microsphere immunoassay (MIA) that uses a disclosed monoclonal antibody (or antigen-binding fragment) conjugated to a microsphere. In other embodiments, the method is an indirect ELISA that uses a disclosed monoclonal antibody (or antigen-binding fragment) bound to a solid support, such as a microtiter plate. In yet other embodiments, the method is an antibody capture ELISA in which a labelled monoclonal antibody (or antigen-binding fragment) disclosed herein is used to detect immune complexes containing HRTV-specific antibodies from a biological sample.

In some embodiments, provided is a method of detecting HRTV-specific antibodies in a biological sample by contacting the biological sample with a microsphere composition under conditions sufficient to allow binding of any HRTV-specific antibodies present in the biological sample to the HRTV N protein, thereby forming a microsphere immune complex; contacting the microsphere immune complex with a labelled secondary antibody; and detecting binding of the secondary antibody to the microsphere immune complex, thereby detecting HRTV-specific antibodies present in the biological sample. In this embodiment, a "microsphere composition" refers to a HRTV N-protein specific monoclonal antibody or binding fragment conjugated to a microsphere, wherein the N-protein specific antibody or binding fragments is also bound to HRTV N protein.

In some examples, the method is a method of detecting HRTV-specific IgM antibodies and the secondary antibody is anti-human IgM. In other examples, the method is a method of detecting HRTV-specific IgG antibodies and the secondary antibody is anti-human IgG. In some examples, the secondary antibody is labelled with a fluorophore. In some examples, a flow cytometer is used to detect binding of the secondary antibody to the microsphere immune complex.

In some embodiments, provided is a method of detecting HRTV-specific antibodies in a biological sample by providing a disclosed monoclonal antibody or antigen-binding fragment bound to a solid support; contacting the antibody-bound solid support with a preparation comprising HRTV N protein under conditions sufficient for the HRTV N protein to bind the monoclonal antibody or antigen-binding fragment to form an antibody-antigen complex; contacting the antibody-antigen complex with the biological sample to allow binding of any HRTV-specific antibodies present in the sample to the HRTV N protein, thereby forming an immune complex; contacting the immune complex with a labelled secondary antibody; and detecting binding of the secondary antibody to the immune complex, thereby detecting HRTV-specific antibodies present in the biological sample.

In some examples, the secondary antibody is labelled with an enzyme and detecting binding of the secondary antibody to the immune complex comprises detecting enzyme activity. In particular examples, the enzyme is horseradish peroxidase or alkaline phosphatase.

In other embodiments, provided is a method of detecting HRTV-specific antibodies in a biological sample that includes providing a secondary antibody bound to a solid support; contacting the antibody-bound solid support with the biological sample under conditions sufficient to allow binding of the secondary antibody to any HRTV-specific antibodies present in the biological sample, thereby forming antibody-antibody complexes; contacting the antibody-antibody complexes with a preparation comprising HRTV N protein under conditions sufficient for the HRTV N protein to bind the HRTV-specific antibodies, thereby forming immune complexes; contacting the immune complexes with an immunoconjugate disclosed herein; and detecting binding of the immunoconjugate to the immune complexes, thereby detecting HRTV-specific antibodies in the biological sample.

In some embodiments of the detection methods disclosed herein, the biological sample is a biological fluid sample. In some examples, the biological fluid sample comprises serum, blood or plasma. In one non-limiting example, the biological sample comprises serum.

Also provided herein are methods of detecting HRTV in an isolated cell or tissue by contacting the cell or tissue with a monoclonal antibody or immunoconjugate disclosed herein and detecting binding of the monoclonal antibody or immunoconjugate to the cell or tissue. An increase in binding of the antibody or immunoconjugate to the cell or tissue as compared to binding of the antibody or immunoconjugate to a control cell or tissue detects HRTV in the cell or tissue. In some embodiments in which a monoclonal antibody (without a label) is used for detection, a labelled secondary antibody is used to detect the presence of HRTV.

A method of treating HRTV infection in a subject by administering to the subject a monoclonal antibody or antigen-binding fragment disclosed herein is also provided by the present disclosure.

Further provided are nucleic acid molecules encoding a VH domain and/or a VL domain of a monoclonal antibody or antigen binding fragment disclosed herein.

In some embodiments, the VH domain coding sequence is at least 80%, at least 85%, at least 90%, at least 95%, at least 96%, at least 97%, at least 98% or at least 99% identical to SEQ ID NO: 1, SEQ ID NO: 5, SEQ ID NO: 9, SEQ ID NO: 13, SEQ ID NO; 17, SEQ ID NO: 21, SEQ ID NO: 25 or SEQ ID NO: 29. In some examples, the VH domain coding sequence comprises SEQ ID NO: 1, SEQ ID NO: 5, SEQ ID NO: 9, SEQ ID NO: 13, SEQ ID NO; 17, SEQ ID NO: 21, SEQ ID NO: 25 or SEQ ID NO: 29.

In some embodiments, the VL domain coding sequence is at least 80%, at least 85%, at least 90%, at least 95%, at least 96%, at least 97%, at least 98% or at least 99% identical to SEQ ID NO: 3, SEQ ID NO: 7, SEQ ID NO: 11, SEQ ID NO: 15, SEQ ID NO: 19, SEQ ID NO: 23, SEQ ID NO: 27 or SEQ ID NO: 31. In some examples, the VL domain coding sequence comprises SEQ ID NO: 3, SEQ ID NO: 7, SEQ ID NO: 11, SEQ ID NO: 15, SEQ ID NO: 19, SEQ ID NO: 23, SEQ ID NO: 27 or SEQ ID NO: 31.

In some embodiments, the nucleic acid molecule is operably linked to a promoter. Vectors comprising the nucleic acid molecules are further provided. Also provided are isolated host cells transformed with the nucleic acid molecules and vectors disclosed herein.

IV. Monoclonal Antibodies and Antigen-Binding Fragments Thereof

The monoclonal antibodies disclosed herein can be of any isotype. The monoclonal antibody can be, for example, an IgM or an IgG antibody, such as IgG$_1$ or an IgG$_2$. The class of an antibody that specifically binds HRTV can be switched with another (for example, IgG can be switched to IgM), according to well-known procedures. Class switching can also be used to convert one IgG subclass to another, such as from IgG$_1$ to IgG$_2$.

Antibody fragments are also encompassed by the present disclosure, such as single-domain antibodies (e.g., VH domain antibodies), Fab, F(ab')$_2$, and Fv. These antibody fragments retain the ability to selectively bind with the antigen. These antigen-binding fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV$_2$), defined as a dimer of a scFv (also known as a "miniantibody"); and (7) VH single-domain antibody, an antibody fragment consisting of the heavy chain variable domain.

Methods of making these fragments are known in the art (see for example, Harlow and Lane, *Antibodies: A Laboratory Manual*, Cold Spring Harbor Laboratory, New York, 1988).

In some cases, antibody fragments can be prepared by proteolytic hydrolysis of the antibody or by expression in a host cell (such as *E. coli*) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the V$_H$ and the V$_L$ regions, and will retain the charge characteristics of the residues in order to preserve the low pI and low toxicity of the molecules Amino acid substitutions (such as at most one, at most two, at most three, at most four, or at most five amino acid substitutions) can be made in the V$_H$ and/or the V$_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

VI. Detection of Heartland Virus-Specific Antibodies

Methods of detecting HRTV-specific antibodies in a biological sample, such as a serum sample, using a HRTV-specific monoclonal antibody, are disclosed herein. Detection assays based on binding of an antigen to an antibody are well known in the art and include, for example, ELISA, microsphere immunoassay (MIA), immunofluorescence assay (IFA), Western blot, fluorescence activated cell sorting (FACS), radioimmunoassay (RIA), immunohistochemistry (IHC) and plaque reduction neutralization test (PRNT). As is well known to one of skill in the art, in some cases the detection assay further includes the step of contacting an antigen-antibody complex with a detection reagent, such as a labeled secondary antibody (e.g., an anti-isotype antibody, such as an anti-IgG antibody), or in the case of a sandwich ELISA, a second antibody that recognizes the same antigen as the first antibody and is labeled for detection. Secondary antibodies can also be conjugated to magnetic beads to allow for magnetic sorting. In other cases, the primary antibody is directly labeled. Directly labeled antibodies can be used for a variety of detection assays, such as FACS. The HRTV-specific antibodies disclosed herein can be used any immune-based detection assay for the diagnosis of HRTV infection. Several exemplary immune-based detection assays are described below.

A. Microsphere Immunoassay (MIA)

Microsphere immunoassays are becoming increasingly popular for laboratory diagnosis of many diseases (Earley et al., *Cytometry* 50:239-242, 2002; Kellar et al., *Cytometry* 45:27-36, 2001). The technology involves the detection and analysis of a reaction (such as an antibody or other ligand) attached to microspheres or beads. The detecting instrument is a simplified flow cytometer, and lasers simultaneously identify the microsphere sets and measure the fluorescence associated with the reaction. The speed at which these tests can be performed and the ability to multiplex make this methodology particularly useful.

A MIA can be used to detect the presence of Heartland virus-specific antibodies in a sample. In some embodiments, microsphere beads are coated with a Heartland virus-specific antibody (such as an antibody produced by a hybridoma cell line disclosed herein) and contacted with HRTV antigen such that the HRTV antigen binds to the microsphere-bound virus-specific antibodies. The microsphere immune complexes are mixed with a serum sample such that antibodies in the sample that are specifically reactive with the HRTV antigen bind the HRTV antigen bound (indirectly) to the microsphere. The bead-bound immune complexes are allowed to react with fluorescent-dye labeled anti-species antibody (such as PE-labeled anti-human IgM or anti-human IgG), and are measured using a microsphere reader (such as a Luminex instrument).

B. IgM Antibody Capture (MAC)-ELISA

For some types of viruses, the host IgM response to infection occurs earlier than that the IgG response, and thus can be used to identify recent infections (Tardei et al., *J Clin Microbiol* 38(6):2232-2239, 2000). MAC-ELISA is typically performed to detect the IgM level in serum samples (Martin et al., *J Clin Microbiol* 38(5):1823-1826, 2000). In these assays, anti-human IgM serves as a capture antibody and is coated onto an appropriate assay plate, such as a multi-well plate. After blocking of the plate, such as with nonfat dry milk, diluted human sera are reacted with the anti-human IgM. Viral antigens, such as infected tissue or cell extracts or recombinant viral proteins, are added to the plates. A virus antigen-specific antibody conjugated to detectable label (for example, an enzyme, such as horseradish peroxidase (HRP)) is then reacted with the immobilized viral antigen. After addition of an appropriate substrate (such as 3,3'5,5' tetra methyl benzidine if HRP is used as the enzyme), reactions are measured using a microplate reader. Serial dilutions of positive sera can be evaluated. The maximum dilution that exhibits positive signal is the titer for the serum. The titer of the MAC-ELISA can be compared with the titers of other tests, such as hemagglutination inhibition tests (HIT) or PRNT. Serum samples can also be tested on control antigen in addition to viral antigen, to reduce the number of false-positive results due to non-specific binding of the serum or other factors (U.S. Patent Application Publication No. 2006/0115896).

C. Indirect ELISA

Indirect ELISAs to detect the presence of virus-specific antibodies are typically carried out by coating a microtiter plate with an antigen-specific antibody (such as a HRTV-specific monoclonal antibody), blocking the plates to prevent non-specific binding to the plate surface, and adding virus antigen to allow binding of the antigen to the virus-specific antibody. After several washes, diluted human sera is added to allow binding of any antibodies present in the sample to the immobilized viral antigens. IgM or IgG antibodies that were present in the sample are then detected using a labelled secondary antibody, such as anti-human IgG or anti-human IgM conjugated to an enzyme (such as alkaline phosphatase or HRP). An appropriate enzyme substrate is then added and the presence of virus-specific antibody is detected by measuring enzyme activity (for example, by measuring fluorescence, optical density or colorimetric absorbance).

D. Lateral Flow Assay (LFA)

Lateral flow immunoassays are another method by which antigen-specific antibodies (or pathogen-specific antigens) can be detected in biological samples. These assays are generally very rapid and enable point of care testing. LFA is performed over a strip, different parts of which are assembled on a plastic backing. These parts are sample application pad, conjugate pad, nitrocellulose membrane and adsorption pad. Nitrocellulose membrane is further divided into test and control lines. Pre-immobilized reagents at different parts of the strip become active upon flow of liquid sample. LEA combines the unique advantages of biorecognition probes and chromatography.

Several designs have been developed for lateral flow assays. Generally LFAs include a porous support strip (such as a strip of cellulose) with a number of separate regions spaced horizontally along the support. The solid support need not be identical in all regions of a strip. Typically, the first region is a sample pad where a biological fluid is applied to flow laterally through the support to the remaining regions. The second region generally contains a labeling moiety that can be bound to the analyte of interest (such as an antibody or protein) in the sample if present. Downstream of the labeling region is a capture or "test" region where the labeled analyte (for example, antibody or peptide) is retained in the strip. It is in this test region where detection is generally performed. In addition to the test region, the strip may contain a control region either in the same flow path as that of the test region, or in a parallel path on the strip. There may also be a reservoir downstream of the various regions to absorb the sample that has traversed the test strip.

LFAs can be direct assays, forming sandwiches in proportion to the level of analyte present, or may be competition assays where analyte in the sample diminishes the amount of label detected in the detection zone. In direct sandwich assays, for example, the sample may be labeled by colored particles that are coupled to affinity reagents such as secondary antibodies the bind HRTV-specific antibodies present in the sample, forming complexes which are then carried to the test region for capture by an additional reagent. The detectable label in the test region will be directly proportional to the level of peptide in the sample.

In competitive assays, the labeling region may contain labeled reagents, for example, that are already coupled to the target analyte (e.g. antibody) or an analog thereof, and the analytes in the sample compete with this labeled material for capture by the capture reagent in the test region. In this case, the detectable label in the test region will be inversely proportional to the quantity of analyte in the sample itself.

Simple visual detection is the most common means of reading an LFA, however, there are commercially available lateral flow readers that can quantitate the detectable label in the test region.

LFAs can be used, for example, to detect antigen-specific antibodies present in a biological sample (such as a serum sample) that specifically recognize HRTV. These assays can also be used to detecting pathogen-specific proteins/peptides present in a biological sample The following examples are provided to illustrate certain particular features and/or embodiments. These examples should not be construed to limit the disclosure to the particular features or embodiments described.

EXAMPLES

Example 1: Heartland Virus Produces a Humoral Response Lacking Virus-Neutralizing Antibody In Vivo Heartland virus (HRTV) is a newly discovered member of the *Phlebovirus* genus in the family Bunyaviridae, presumably transmitted by ticks to humans causing severe disease characterized by fever, leukopenia and thrombocytopenia (McMullan et al., N Engl J Med 367: 834-841, 2012). It is closely related to severe fever with thrombocytopenia syndrome virus (SFTSV) from China with case fatality rates as high as 30% in outbreaks. Since 2009, only 8 cases of HRTV have been documented. Little is known about HRTV and currently the only diagnostic tests are RT-PCR and plaque reduction neutralization test (PRNT). In the study described below, mice were experimentally inoculated in order to better understand the virulence, pathology and subsequent immune response to HRTV. Monoclonal antibodies were also produced in order to develop serological diagnostic tests.

Methods

Three-week old C57BL/6 mice were inoculated with $10^4$ PFU, boosted with $10^4$ PFU on 28 days post infection (DPI), and bled at 42 DPI to determine antibody titers. Three-week old α, β and γ interferon-receptor deficient AG129 mice were inoculated with $10^4$ to $10^0$ PFU and observed through day 30 to determine the $LD_{50}$ dose. AG129 mice surviving challenge with $10^2$ PFU were boosted 30 DPI, and spleens were harvested 4 days later for hybridoma production. Viremias were determined by plaque assay and $PRNT_{80}$ were performed on Vero E6 cells. Serum antibody and monoclonal antibody titers were determined by ELISA with purified virus coated directly to the plate. Protein specificity was determined by running purified HRTV on 4-12% Bis/Tris gels with (ME+) or without (ME−) reducing agent (β-mercaptoethanol). Cross-reactivity was determined by immunofluorescent assay (IFA) on SFTSV-infected Vero cells.

Results

All C57BL/6 mice survived challenge with $10^4$ PFU HRTV, and no viremia was detected. All AG129 mice succumbed to infection with $10^4$ PFU HRTV. An $LD_{50}$ was calculated to be 9 PFU. Hepatic hemorrhagic lesions and enlarged pale spleens were observed in AG129 mice that succumbed to infection Immunohistochemistry showed antigen in hematopoietic cells in the spleen, interstitial mononuclear cells in the kidney and Kupffer/sinusoidal cells in the liver.

Low to no detectable neutralizing antibody was detected in C57BL/6 mice; however, high ELISA antibody titers were observed (Table 1) and antibodies specific for Gn/Gc and N were detected. In infected AG129 mice, no detectable neutralizing antibody was found with any dose; however, high ELISA antibody titers were detected (Table 1), as well as antibodies specific for Gn/Gc and N.

TABLE 1

HRTV-Specific Antibody Responses in Surviving Mice

| Mice[a] | HRTV Dose (PFU) | Geometric mean reciprocal $PRNT_{80}$ ($\log_{10}$) | Geometric mean reciprocal ELISA titer ($\log_{10}$) | Mice with ELISA Ab titers >2.70 | Survivors/total |
|---|---|---|---|---|---|
| C57BL/6 | 10⁴ | 1.13 (0.91)[b] | 4.47 (0.42) | 15/15 | 16/16 |
| AG129 | 10³ | >1.00 (0) | 4.13 (2.02) | 1/2 | 3/15 |
| AG129 | 10² | >1.00 (0) | 3.89 (1.68) | 1/2 | 2/14 |
| AG129 | 10¹ | >1.00 (0) | 3.49 (1.37) | 1/3 | 3/15 |
| AG129 | 10⁰ | >1.00 (0) | 2.74 (0.117) | 1/10 | 11/13 |

[a]3-week old C57BL/6 and AG129 mice were inoculated intraperitoneally with 0.1 ml of HRTV. C57BL/6 mice were bled on day 42, and surviving AG129 mice were bled on day 30 to determine PRNT and ELISA antibody titers.
[b]Standard deviation in parentheses.

Twenty hybridomas were produced using splenocytes from HRTV-infected AG129 mice. Seven MAbs with the highest reactivity in ELISA were purified and characterized (Table 2). All 7 MAbs had high endpoint ELISA titers. The MAbs were non-neutralizing and specific to linear epitopes on the nucleocapsid protein. No cross-reactivity to SFTSV antigen was detected.

TABLE 2

Serological and Biological Characteristics of Anti-HRTV MAbs

| MAb | Isotype | ELISA[a] | Reciprocal $PRNT_{80}$[b] | −ME[c] | +ME[c] | Cross-reactivity with SFTSV[d] |
|---|---|---|---|---|---|---|
| 2AG8 | IgG2a | 0.381 | >10 | N | N | NEG |
| 2AG9 | IgG2a | 1.526 | >10 | N | N | NEG |
| 2BA2 | IgG1 | 39.06 | >10 | N | N | NEG |
| 2BB10 | IgG1 | 937.5 | >10 | N | N | NEG |
| 2BB5 | IgG3 | 0.156 | >10 | N | N | NEG |
| 2BB7 | IgG2b | 24.41 | >10 | N | N | NEG |
| 2BB8 | IgG2a | 0.610 | >10 | N | N | NEG |

[a]ELISA endpoint titers expressed as ng/ml.
[b]PRNT endpoint titers expressed as ng/ml.
[c]Protein specificities (by immunoblot): N, nucleocapsid.
[d]Cross-reactivity with SFTSV antigen determined by IFA on SFTSV-infected Vero cells.

Conclusion

Adult C57BL/6 mice did not succumb to HRTV infection; however, they did develop an anti-viral humoral response characterized by high antibody titers with low or no neutralizing antibody. Similar results have been found with SFTSV-infected C57BL/6 mice (Jin et al., Proc Natl Acad Sci USA 109:10053-10058, 2012). In contrast, interferon receptor-deficient AG129 mice developed illness similar to human clinical disease. No neutralizing antibody was detected in AG129 mice that survived HRTV infection; however, virus-specific antibody titers were reasonably high. Similarly, adult α/β interferon receptor-deficient A129 mice were found to be highly susceptible to SFSTV infection with the most heavily infected tissues being in the mesenteric lymph nodes and spleen of infected mice (Liu et al., *J Virol* 88:1781-1786, 2014). Of the 20 hybridomas developed using splenocytes from HRTV-infected AG129 mice, seven were highly reactive by ELISA. These MAbs were nucleocapsid-specific and non-neutralizing. The majority of anti-SFTSV human and murine MAbs developed have been nucleocapsid-specific and non-neutralizing (Yu et al., *PLoS One* 7: e38291, 2012; Guo et al., *Clin Vaccine Immunol* 20: 1426-1432, 2013). The nucleocapsid protein has been shown to be the immunodominant viral protein in other phleboviral infections with Rift Valley fever virus and Toscana virus (Martin-Folgar et al., *MAbs* 2: 275-284, 2010; Magurano and Nicoletti, *Clin Diagn Lab Immunol* 6: 55-60, 1999). Serologic diagnostic assays that do not rely on the detection of neutralizing antibody and BSL-3 containment are needed. An IgM antibody capture ELISA (MAC-ELISA) and LUMINEX™ assay for the detection of HRTV-specific IgM and IgG using the disclosed HRTV-specific MAbs are described herein (see Example 3).

Example 2: Monoclonal Antibodies Directed Against the Nucleoprotein of Heartland Virus Diagnostic assays for the detection of HRTV is currently limited to the detection of viral RNA by RT-PCR and the detection of neutralizing antibody by plaque reduction neutralization test (PRNT). In order to develop diagnostic assays able to detect both recent and past infections and to assess the disease burden of HRTV infection in the United States, anti-HRTV murine MAbs were developed and characterized. Interferon-receptor deficient AG129 mice approximately 3 weeks old were inoculated intraperitoneally (IP) with 100 plaque forming units (PFU) of HRTV strain MO-4. Thirty days later, mice were bled and boosted with another 100 PFU of HRTV MO-4 IP. Splenocytes were harvested 4 days after the last inoculation for fusions with the mouse myeloma cell line P3X63Ag8.653 using the CLONACELL™-HY Hybridoma cloning kit (StemCell Technologies).

This is the first report of the use of activated B cells from AG129 mice for the development of hybridomas. B-cell hybridoma clones are generally made by isolating activated B cells from the spleen of an immunized BALB/c mouse or mouse with a compatible major histocompatibility complex (MHC) haplotype (H2$^d$) and fusing with a myeloma cell with the same haplotype. In this case, AG129 mice were used as B cell donors which have a different MHC haplotype (H2$^b$) from the P3X63Ag8.653 myeloma cells used for fusions. While the use of BALB/c mice may be appropriate for most infectious agents, some pathogens may be unable to mount a robust immune response. Utilizing AG129 mice for hybridoma development may be more appealing in these situations.

After fusions, hybridomas were grown in high-glucose Dulbecco minimal essential medium supplemented with L-glutamine, 10% low IgG fetal bovine serum, 1 mM sodium pyruvate, 2 mM L-glutamine, 0.15% sodium bicarbonate, 100 U/ml penicillin G sodium, 100 µg/ml streptomycin sulfate, and 0.1 mM nonessential amino acids. MAbs were purified from highly concentrated culture media using protein-A SEPHAROSE™ (GE Healthcare) according to the manufacturer's instructions. Purified MAbs were dialyzed against PBS and the concentration was measured by Bradford protein assay.

Sera from infected mice taken on days 30 and 34 post-infection were tested by enzyme-linked immunosorbent assay (ELISA) using purified HRTV at a dilution of 0.06 µg/well coated overnight at 4° C. to 96-well plates in 50 mM sodium carbonate/50 mM sodium bicarbonate buffer, pH 9.6. Plates were washed five times in PBS/0.05% Tween before non-specific binding sites were blocked with Starting Block (Pierce) and sera diluted in PBS were incubated on the plates for one hour at 37° C. Plates were washed again before goat anti-mouse conjugated to horseradish peroxidase diluted 1:5000 in PBS was incubated on the plates. After plates were washed a final time, reactions were developed using TMB K-blue substrate (KPL) and stopped with the addition of 1N $H_2SO_4$ before being read at 450 nm. On day 30, mouse 1 and mouse 2 had ELISA endpoint titers of <2.70 $\log_{10}$ and ≥4.60 $\log_{10}$, respectively, indicating that mouse 1 did not develop an infection after the first inoculation. On day 34, those ELISA titers increased to 2.70 $\log_{10}$ and 5.56 $\log_{10}$, respectively, while $PRNT_{80}$ titers on Vero cells were 1.90 $\log_{10}$ and 2.51 $\log_{10}$, respectively (Table 3).

TABLE 3

HRTV-specific antibody responses in AG129 mice following primary and secondary immunizations with HRTV

| Mouse No. | Geometric mean reciprocal ELISA titer ($\log_{10}$) | | Geometric mea reciprocal $PRNT_{80}$ ($\log_{10}$) |
|---|---|---|---|
| | 30 DPI* | 34 DPI | 34 DPI |
| 1 | <2.70 | 2.70 | 1.90 |
| 2 | ≥4.6 | 5.56 | 2.51 |

*Days post-infection.

To determine the viral protein specificity of the antibody response, purified HRTV (5 µg/well) was run on a 4-12% Bis-Tris polyacrylamide gel (Life Technologies) under reducing conditions. Proteins were blotted electrophoretically from the gels onto nitrocellulose membranes and washed for 15 minutes in PBS/0.1% Tween wash buffer. Non-specific binding sites were blocked with 10% goat serum in PBS for 1 hour while rocking. Sera diluted 1:200 were incubated with the membrane for 1 hour with gentle rocking. Membranes were washed again before goat anti-mouse conjugated to alkaline phosphatase (Jackson ImmunoResearch) was diluted 1:200 and incubated on the membrane for 1 hour with gentle rocking. Membranes were washed and BCIP/NBT phosphatase substrate (KPL) was added until a color change appeared. Even though neutralizing antibody titers were detected for both mice, only mouse 2 produced IgG anti-glycoprotein (Gn and Gc) and anti-N antibody to HRTV detectable by Western blot by day 34 (FIG. 1).

Twenty hybridoma clones secreting anti-HRTV MAb were isolated from fusions. Nineteen of these were from fusions using splenocytes from mouse 2, while only one hybridoma clone was isolated from fusions using splenocytes from mouse 1. Twelve of the hybridoma clones were of varying IgG isotypes, while the other 8 were IgM (Table 4). Nine of the IgG MAbs were titrated by ELISA as previously described with starting concentrations of purified MAbs beginning at 10 µg/ml. An optical density (OD) of two times the background was considered a positive result and endpoints were expressed in ng/ml. The MAbs with the highest reactivities by ELISA were 2BB5, 2AG8, 2BB8 and 2AG9 with endpoint concentrations of 0.156, 0.381, 0.610 and 1.526 ng/ml, respectively. The MAbs with moderate reactivities by ELISA were 2BB7, 2BA2, and 2BB10 with endpoint concentrations of 24.41, 39.06 and 937.5 ng/ml.

Two MAbs (2AF11 and 2BB6) had the lowest ELISA reactivities (10 µg/ml endpoints) (Table 4).

To assess whether these MAbs could neutralize virus in vitro, purified MAbs were tested in a PRNT with HRTV. One PFU of HRTV MO-4 were incubated with equal amounts of serial two-fold dilutions of purified antibody starting at 10 µg/ml for 1 hour at 37° C. Six-well plates of Vero cells were then inoculated with the virus-antibody mixtures and incubated at 37° C. with 5% $CO_2$ for 1 hour after which cells were overlaid with 3 ml of medium containing 1% SeaKem LE agarose (FMC BioProducts) in nutrient medium (0.165% lactalbumin hydrolysate, 0.033% yeast extract, Earle's balanced salt solution and 2% FBS). Following incubation at 37° C. for 7 days, a second overlay containing an additional 80 µg of neutral red vital stain (GIBCO-BRL) per ml was added. Plaques were counted on days 9 and 10. None of the MAbs were found to neutralize virus in vitro when tested by plaque reduction neutralization test using an 80% reduction in plaque formation as significant ($PRNT_{80}$) (Table 4).

Viral glycoprotein specificity for these MAbs was determined by immunoblot with or without the reducing agent, β-mercaptoethanol (ME). All anti-HRTV MAbs reacted specifically with the N protein which is approximately 20 KDa in mass. These MAbs were reactive under reducing and non-reducing conditions suggesting that all 9 MAbs recognize linear epitopes on the N protein (Table 4).

In order to determine the cross-reactivity of anti-HRTV MAbs with SFTSV, Vero cells were infected with SFTSV, harvested 5 days after infection and fixed to 12-well glass slides in 70% acetone in PBS. MAbs were added in doubling dilutions (20 µl/well) to the wells of the slide and incubated at 37° C. for 30 minutes. Slides were washed three times in PBS before goat anti-mouse conjugated to fluorescein isothiocyanate (FITC) (Invitrogen) diluted 1:200 in PBS was added (20 µl/well) and incubated at 37° C. for 30 minutes. Only MAb 2AF11 was found to be cross-reactive with SFTSV with an endpoint titer of 1 µg/ml (Table 4).

TABLE 4

Serological and Biological Characteristics of anti-HRTV MAbs

| MAb | Isotype | ELISA endpoint[a] | Reciprocal $PRNT_{80}$[b] | −ME | +ME | Cross-reactivity with SFTSV[d] |
|---|---|---|---|---|---|---|
| 2BB5 | IgG3 | 0.156 | >10 | N | N | NEG[e] |
| 2AG8 | IgG2a | 0.381 | >10 | N | N | NEG |
| 2BB8 | IgG2a | 0.610 | >10 | N | N | NEG |
| 2AG9 | IgG2a | 1.526 | >10 | N | N | NEG |
| 2BB7 | IgG2b | 24.41 | >10 | N | N | NEG |
| 2BA2 | IgG1 | 39.06 | >10 | N | N | NEG |
| 2BB10 | IgG1 | 937.5 | >10 | N | N | NEG |
| 2AF11 | IgG2a | $10^4$ | >10 | N | N | 1.0 |
| 2BB6 | IgG2b | $10^4$ | >10 | N | N | NEG |

[a] ELISA endpoint titers expressed as ng/ml.
[b] PRNT endpoint titers expressed as µg/ml.
[c] Protein specificities (by immunoblot): N, nucleocapsid.
[d] Cross-reactivity with SFTSV antigen determined by IFA on SFTSV-infected Vero cells. IFA endpoint titers expressed as µg/ml.
[e] Negative reactivity with SFTSV-infected cells.

This study reports the first generation of a panel of murine monoclonal antibodies directed to HRTV as well as the importance of the N protein in immunogenicity to HRTV infection. The majority of anti-SFTSV human and murine MAbs developed have been nucleocapsid-specific and non-neutralizing (Yu et al., PLoS One 7: e38291, 2012; Guo et al., Clin Vaccine Immunol 20: 1426-1432, 2013). The exception has been a human MAb (hMAb) recognizing a linear epitope in the ectodomain of Gn able to neutralize virus in vitro by blocking virus-cell mediated attachment (Guo et al., Clin Vaccine Immunol 20: 1426-1432, 2013). The N protein has also been shown to be the immunodominant protein in other phleboviral infections including Rift Valley fever virus (RFTV) and Toscana (TOSV) viruses (Martin-Folgar et al., MAbs 2: 275-284, 2010; Magurano and Nicoletti, Clin Diagn Lab Immunol 6: 55-60, 1999). It is highly conserved in the Bunyaviridae family and is the most abundantly expressed viral protein in virus-infected cells (Magurano and Nicoletti, Clin Diagn Lab Immunol 6: 55-60, 1999; Schwarz et al., J Med Virol 49: 83-86, 1996; Swanepoel et al., J Hyg (Lond) 97: 317-329, 1986). Even though the N protein does not produce neutralizing antibody, MAbs directed against this antigen can be protective in vivo against RVFV and Hantaan viral infections (Boshra et al., Vaccine 29: 4469-4475, 2011; Jansen van Vuren et al., PLoS One 6: e25027, 2011; Nakamura et al., Arch Virol 86: 109-120, 1985; Yoshimatsu et al., Arch Virol 130: 365-376, 1993). While neutralizing antibodies in bunyaviral infections are directed to the Gn or Gc glycoproteins, these antibodies may be harder to isolate since they usually recognize conformationally-dependent epitopes requiring higher binding avidities (Magurano and Nicoletti, Clin Diagn Lab Immunol 6: 55-60, 1999; Besselaar and Blackburn, Arch Virol 121: 111-124, 1991; Lundkvist et al., Arch Virol 130: 121-130, 1993).

Serologic diagnostic assays that do not rely on the detection of neutralizing antibody and BSL-3 containment are needed for the detection of HRTV-specific IgM and IgG. Recombinant N protein has been used in diagnostic applications for phleboviruses including RVFV and SFTSV (Paweska et al., Vet Microbiol 127: 21-28, 2008; Paweska et al., J Virol Methods 127: 10-18, 2005; Jiao et al., J Clin Microbiol 50: 372-377, 2012). An assay for the detection of total anti-HRTV antibody reactivity in serum samples may be more beneficial than neutralization assays that require special containment. The MAbs described herein were evaluated for their inclusion in microsphere immunoassays and ELISAs for the detection of HRTV-specific IgM and IgG in human infections (see Example 3).

Example 3: Development of IgM and IgG Microsphere Immunoassays for Heartland Virus Bunyaviruses are a significant cause of human illness world-wide, with the most common in the United States being La Crosse encephalitis virus (LACV), of the genus Orthobunyavirus. Phleboviruses possess large (L), medium (M) and small (S) genomic segments that encode genes for RNA-dependent RNA polymerase, envelope glycoproteins (Gn and Gc) and a nucleocapsid protein, respectively. Diagnostic methods for LACV were unsuitable for HRTV, and methods were developed using sequence information and virus isolates to generate reagents to aid in laboratory diagnosis. An RT-PCR method was devised using primers and probes that targeted the S segment (Lambert and Lanciotti, J Clin Microbiol 47:2398-2404, 2009). An IgG assay using inactivated virus-infected cell lysate was also developed (McMullan et al., N Engl J Med 367: 834-841, 2012). These tests were followed by the traditional serological method of PRNT (Lindsey et al., J Clin Microbiol 4:503-510, 1976).

To date, there are 9 confirmed cases of HRTV have been identified in the States of Missouri, Oklahoma and Tennessee (Pastula et al., MMWR Morb Mortal Wkly Rep 63:270-271, 2014). As local health departments were made aware of this newly discovered virus, and studies designed to identify potentially-infected patients were developed, the need for rapid and reliable serological assays increased. The lack of an IgM assay precluded the distinction of recent infections from those of past infections, when RNA was not present in acute patient samples. Immunofluorescence assays (IFAs) are inconsistent with the less subjective current methodologies such as ELISA and MIAs. Development of HRTV MIAs for detection of IgM and IgG are described herein; these assays overcome many of the shortfalls of the existing methods.

Anonymized serum samples previously received for laboratory diagnosis were used in the development and validation of these assays. Serum samples submitted for HRTV testing were from patients who had clinical and circumstantial presentations that were consistent with those described for HRTV, and who were accordingly enrolled in studies that were designed to investigate this virus. Serum specimens from patients previously diagnosed with non-HRTV infections or non-arboviral infections were also used. Data from 91 serum samples enrolled in a HRTV-related study were included, where results from an additional 49 blood or tissue samples that were previously tested by molecular or isolation methods only, were included in the analyses. A further cohort of 40 non-HRTV-related samples from the DVBD archives were included.

Tissue culture-derived HRTV antigen was produced in Vero cells and harvested at day 10 post-infection. After centrifugal clarification, virus was inactivated using 0.1% beta-propiolactone and checked for absence of infectivity (Goodman et al., *J Virol Methods* 208:66-78, 2014). Antigen preparations were stored frozen at −70° C. until use. The same procedure was performed for non-infected Vero cells to produce normal antigen to serve as a control in the MIAs.

Diagnostic results from the DVBD database for the samples were used to confirm those of the MIAs. Where multiple samples taken from a single patient were received, the most acute sample, preferably whole blood, was tested by RT-PCR or virus isolation, or both. Viral RNA was extracted using a Qiagen QIAmp Viral RNA extraction kit (Qiagen, Inc, Valencia, Calif.) according to the manufacturer's instructions and RT-PCR was performed according to Savage et al. (*Am J Trop Med Hyg* 89:445-452, 2013. Virus isolation was attempted for a few samples in Vero E6 cells and cytopathic effect was checked daily for up to 12 days. To confirm HRTV antibody presence, PRNTs were performed using Vero cells (Lindsey et al., *J Clin Microbiol* 4:503-510, 1976). A double overlay system was used where the second overlay with neutral red was applied six days after the cells were infected, and plaques were read over the following two days. Ninety percent plaque reduction compared to the negative control indicated a positive reaction.

To obtain a comparative measure of IgM content, samples were tested using IFA (Storch, "Diagnostic virology," Lippincott, Williams and Wilkins, Philadelphia, Pa., 2007) with HRTV (strain M12-66) in Vero E6 cells that were harvested six days post-inoculation. A minimum 4-fold difference between the highest serum dilution to fluoresce on virus-containing cells and non-infected cells indicated a positive result. IgG ELISA results were compared to those of the IgG MIA. Inactivated virus-infected cell lysate antigen was used to coat 96-well plates at a 1:1000 dilution in PBS with an overnight incubation at 4° C. Serum dilutions were added at a 1:1000 dilution in 5% milk block and incubated for 1 hour at 37° C. Anti-HRTV IgG was detected with anti-human IgG horseradish peroxidase (HRP) (Jackson Immunoresearch) at 1:1000 for 1 hour at 37° C. Reactions were visualized using TMB substrate (Neogen, Lansing, Mich.), stopped with 1 N $H_2SO_4$ and read at 450 nm.

MIAs were developed to detect IgM and IgG antibodies to HRTV. Murine MAbs to HRTV were generated in AG129 mice (van den Broek et al., *J Virol* 69:4792-4796, 1995) and characterized (see Examples 1 and 2). After purification using protein A SEPHAROSE™ (GE Healthcare Bio-Sciences, Piscataway, N.J.), MAb 2BB5 (a non-neutralizing IgG3 isotype that recognizes nucleocapsid protein) was covalently bound to individual MICROPLEX™ microsphere sets (Luminex Corp, Austin, Tex.) using standard carbodiimide coupling at a rate of 25 μg per 5.4 million microspheres as described previously (Johnson et al., *Clin Diagn Lab Immunol* 12:566-574, 2005). Microspheres were adjusted to $5 \times 10^6$/ml and the HRTV antigen reaction was titrated with the beads to determine optimal signal-to-noise ratio in the IgM and IgG tests. Final volumes of 100 μl antigen (IgM assay) and 12.5 μl antigen (IgG assay) were added to 0.25 million antibody-coupled microspheres per 0.5 ml in Antibody Stabilizer (Boca Scientific, Boca Raton, Fla.) in amber vials and rotated for 1 hour at room temperature, then stored at 4° C. until use. Previous experience has shown that microspheres prepared in this manner can be used from two days to five months (Basile et al., *Clin Vaccine Immunol* 17:56-61, 2010) after addition of antigen to the microspheres. The same was done using tissue culture-derived normal antigen to serve as a negative antigen control.

Positive and negative control sera were identified using IFA (for IgM) and IgG ELISA (for IgG). Microspheres were diluted 1:10 in Low Cross Buffer (Boca Scientific, Boca Raton, Fla.) and 50 μl per well (2500 microspheres) was added to a pre-wet 96-well filter plate (Millipore Corp, Billerica, Mass.). Wells were washed 2× with 100 μl PBS using a vacuum filtration manifold. Control sera for the IgM test was IgG-depleted as previously described (Johnson et al., *Clin Diagn Lab Immunol* 12:566-574, 2005) and diluted 1:400 in 50% low cross buffer (LCB) (Boca Scientific, Boca Raton, Fla.) and 50 μl was added to the washed microspheres. No depletion was necessary for the IgG controls, which were diluted at 1:400 in 50% LCB. Sera in the IgM test were co-incubated with 50 μl/well anti-human IgM-red-phycoerythrin (R-PE) at 4 μg/ml of 50% LCB for 1.5 hours at room temperature. The plate was covered with foil to protect the microspheres from being bleached and were kept in a state of suspension on a shaking platform. Wells were washed 2× with 100 μl PBS, resuspended in 100 μl PBS and read on a BioPlex 100 (Biorad, Hercules, Calif.). For the IgG test, sera were added to the washed antigen/microspheres and incubated with shaking for 45 minutes, washed 2×, then 50 μl anti-human IgG-RPE in 50% LCB was added to the wells. After a further 15 minutes of incubation, wells were treated and read in the same manner as for IgM. Readings were based on 50 μl of sample with doublet-discriminator gates set at default, and median fluorescent intensity (MFI) was calculated based on a minimum of 50 microspheres per set per sample.

Samples were anonymized and tested in the MIAs, where MFIs and P/Ns (MFI of test serum reacted on viral antigen/mean MFI of 3 negative control sera) were compared to the reference results.

Figure 2:
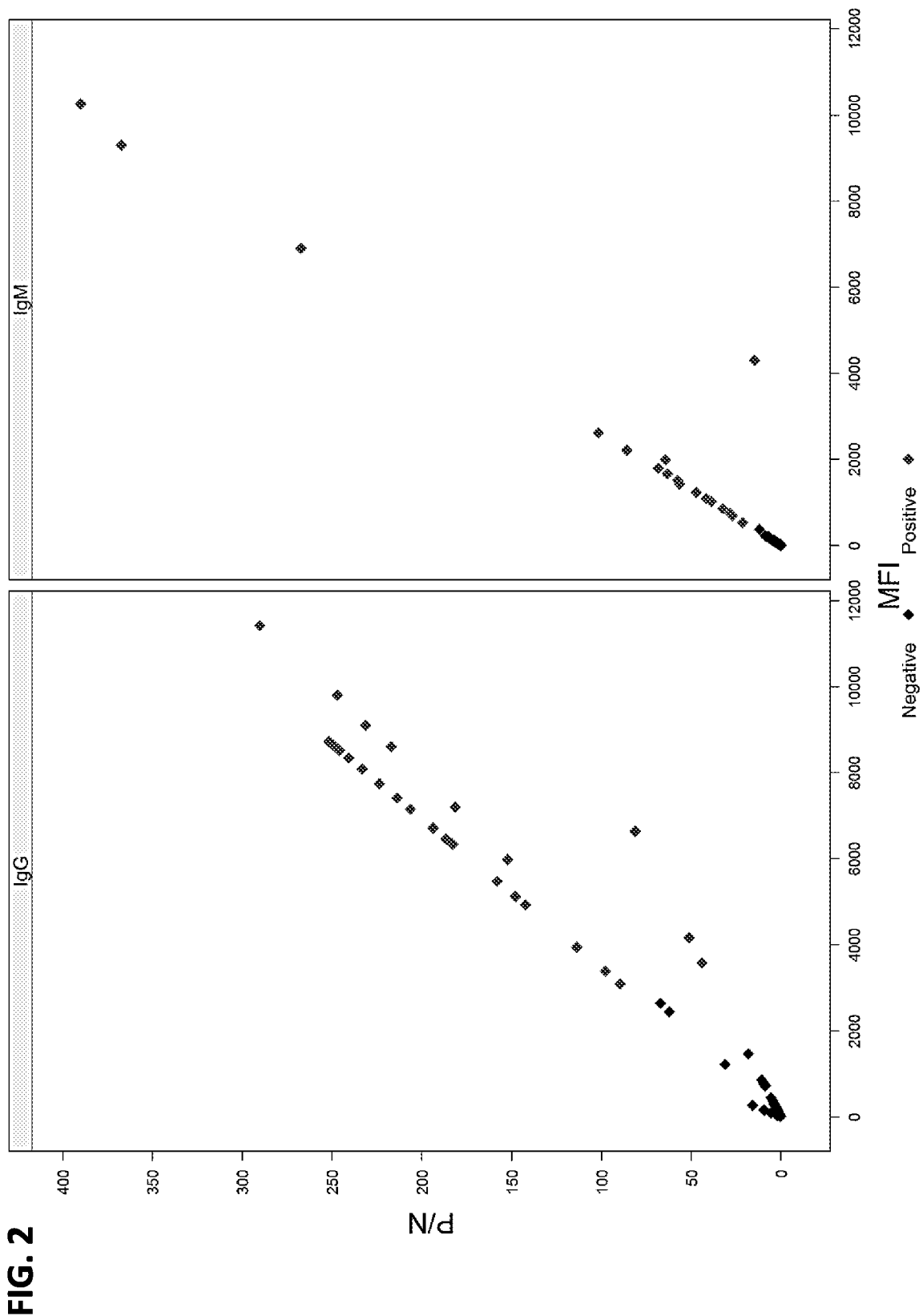
FIG. 2 is a graph showing a comparison of IgM and IgG MIA median fluorescent intensity (MFI) versus P/N values.

To derive the MIA cutoffs from the results of the US and MO HRTV study samples, ROC analysis was performed using IFA results for "truth" versus the IgM MIA MFI values. This yielded a cutoff of 538. The cutoff derived using IFA versus P/N was 14.8. A combination of these cutoffs was chosen to identify positives, equivocals and negatives, where samples with both MFIs≥538 and P/N≥14.8 were positive; where either MFI≥538 OR P/N≥14.8 were equivocal, and where MFI<538 and P/N<14.8 were negative. Similarly, ROC analysis performed using PRNT results for "truth" versus the IgG MIA MFI values yielded a cutoff of 3101. The cutoff derived using PRNT versus P/N was 51.1. A combination of these cutoffs was chosen to identify positives, equivocals and negatives, where samples with both MFIs≥3101 and P/N≥51.1 were positive; where either MFI≥3101 OR P/N≥51.1 were equivocal, and where MFI<3101 and P/N<51.1 were negative. Comparisons of P/N and MFI are charted in FIG. 2.

Because all the available samples were used to derive the cut-offs, it was not possible to validate the cut-offs on an independent sample set. As a substitute, bootstrap analyses (Davison, "Bootstrap methods and their applications," Cambridge Press, Cambridge, 1997) were performed to produce a numerical validation on the original set to produce sensitivity, specificity and 95% confidence intervals, using an S-plus based software (Canty, "Boot: Bootstrap R (S-Plus) Functions," R Package version 1.3-13, 2014). Results are listed in Table 5.

TABLE 5

Cutoffs and percent specificity and sensitivity data for HRTV IgM and IgG MIAs

| Test | Cutoff | ROC cutoff Sensitivity | Specificity |
|---|---|---|---|
| IgM MFI | 538 | 100 (100, 100) | 100 (100, 100) |
| IgM P/N | 14.8 | 100 (100, 100) | 100 (100, 100) |
| IgG MFI | 3101 | 100 (100, 100) | 100 (100, 100) |
| IgG P/N | 51.1 | 96.7 (82.4, 100) | 97.6 (90.3, 100) |

Accuracy was 100% for both IgM and IgG assays based upon the MFI cutoffs, and was 100% using P/N for the IgM assay; 97.4% for the IgG assay. As the tests are incorporated into the diagnostic algorithm, lower cutoffs than these (MFI 500; P/N 10 for IgM and MFI 2000; P/N 20 for IgG) will be used to ensure that low positives are not missed. PRNT will remain as the confirmatory test for all positive samples, thus weeding out false positives among the low positive, equivocal, and background responders in the MIA.

Repeatability within the plate (% CV) and reproducibility across different plates with samples prepared on different days were determined for both tests. Precision analysis using eight samples ranging from high positive to low negative was performed using 12 replicates of the samples within a single plate. The % CV of the viral antigen MFI averaged 15% for the IgM HRTV MIA and 12% for the IgG HRTV MIA. For between-plate precision analysis, the same eight samples were prepared for testing and applied to the IgM and IgG MIAs on six different days. The CV of the viral antigen MFI averaged 18% for the IgM HRTV MIA and 7% for the IgG HRTV MIA.

Samples from confirmed cases of non-HRTV arboviral disease were tested in the HRTV IgM and IgG MIAs to determine if cross-reactivity might exist. Eight samples were IgM and IgG positive to each of the following viruses: La Crosse virus (LACY), eastern equine encephalitis virus (EEEV), West Nile virus (WNV) and Powassan virus (POWV). These arboviruses are all endemic in Missouri and the Midwestern United States. A total of 32 previously-tested diagnostic specimens showed no reaction with the HRTV antigens in either test, indicating a lack of cross-reactivity. The anti-virus antibodies tested were to an alphavirus, two flaviviruses and a California serogroup bunyavirus. Powassan virus is the only tick-borne virus that was investigated for cross-reactivity in the MIAs. Recently, Bourbon virus (Kosoy et al., *Emerg Infect Dis* 21(5):760-764, 2015) was newly discovered in a patient from Missouri. It is of the genus *Thogotovirus* (family Orthomyxoviridae) and is thought to be tick-borne. The patient was initially tested for HRTV and found to be negative; subsequent testing of sera using the MIA assays produced the same negative result, indicating a lack of cross-reactivity with this virus.

All samples tested belonged to a series of 2-4 for the individual patient, and complete results for molecular and serological assays for the 24 patients who were diagnosed with either current or past HRTV infections are shown in FIGS. 3A-3C. In current infections, IgM and IgG were both detectable using the MIAs as early as four days post-onset and as late as day 95, which was true also of the PRNT. Samples outside of this range to investigate the longevity of the antibodies were unavailable. By comparison, RT-PCR was capable of detecting RNA to HRTV in samples collected between four and 15 days after onset of symptoms. Determination of IgM presence using IFA is subjective and is not a method of choice. The addition of a viable non-subjective HRTV IgM assay such as the HRTV IgM MIA to the current repertoire of tests will allow for current infections for which RNA-containing samples are unavailable to be distinguished from past infections by showing an absence of IgM.

Similarly, the HRTV IgG assay has advantages over the current IgG ELISA, which is based upon cell lysate antigen and has shown some inconsistencies. Both MIAs are considerably faster and easier to set up than the IFA and IgG ELISAs. The use of MAbs to capture the antigen on the microspheres is a tool that is successfully employed here to alleviate the requirement for recombinant or purified viral protein, which normally is needed if the protein is to be directly linked to the microspheres. As knowledge of the geographic distribution of HRTV is gained, there may be a need to incorporate HRTV testing at some of the U.S. State Health laboratories. HRTV will likely become part of the differential diagnosis for patients with a history of tick-bite in areas with known HRTV activity, or with obvious leukopenia and thrombocytopenia. Luminex instruments are in use at many of these labs and therefore is a suitable platform for those who wish to add HRTV testing to their menus of screening methods. The efficiency with which the HRTV MIAs can be performed will simplify any serosurveillance in the human population. In addition, the HRTV IgG MIA can easily be modified to test for antibodies in wildlife populations, by using biotin to label the serum antibodies (Basile et al., *Clin Vaccine Immunol* 17:56-61, 2010). The MIAs proved to be accurate and precise, and will be a useful screening tool for HRTV.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated monoclonal antibody specific for the nucleocapsid (N) protein of Heartland virus (HRTV), or an antigen-binding fragment thereof, wherein the monoclonal antibody or antigen-binding fragment comprises a variable heavy (VH) domain and a variable light (VL) domain, wherein the VH and VL domains respectively comprise the complementarity determining region (CDR) sequences of:

SEQ ID NO: 2 and SEQ ID NO: 4;
SEQ ID NO: 6 and SEQ ID NO: 8;
SEQ ID NO: 10 and SEQ ID NO: 12;
SEQ ID NO: 14 and SEQ ID NO: 16;
SEQ ID NO: 18 and SEQ ID NO: 20;
SEQ ID NO: 22 and SEQ ID NO: 24;
SEQ ID NO: 26 and SEQ ID NO: 28; or
SEQ ID NO: 30 and SEQ ID NO: 32.

2. The monoclonal antibody or antigen-binding fragment of claim 1, wherein the CDR sequences are CDR sequences determined by IMGT.

3. The monoclonal antibody or antigen-binding fragment of claim 2, wherein:
the VH domain comprises residues 26-35, 53-59 and 98-111 of SEQ ID NO: 2 and the VL domain comprises residues 27-32, 50-52 and 89-97 of SEQ ID NO: 4;
the VH domain comprises residues 25-33, 50-57 and 96-106 of SEQ ID NO: 6 and the VL domain comprises residues 27-32, 50-52 and 89-97 of SEQ ID NO: 8;
the VH domain comprises residues 17-24, 42-49 and 88-99 of SEQ ID NO: 10 and the VL domain comprises residues 27-31, 49-51 and 88-96 of SEQ ID NO: 12;
the VH domain comprises residues 25-33, 51-57 and 96-107 of SEQ ID NO: 14 and the VL domain comprises residues 27-32, 50-53 and 89-97 of SEQ ID NO: 16;
the VH domain comprises residues 26-33, 51-60 and 99-109 of SEQ ID NO: 18 and the VL domain comprises residues 27-31, 49-51 and 88-96 of SEQ ID NO: 20;
the VH domain comprises residues 26-34, 52-58 and 97-105 of SEQ ID NO: 22 and the VL domain comprises residues 27-31, 49-51 and 88-96 of SEQ ID NO: 24;
the VH domain comprises residues 26-33, 51-58 and 97-106 of SEQ ID NO: 26 and the VL domain comprises residues 27-32, 50-52 and 89-97 of SEQ ID NO: 28; or
the VH domain comprises residues 26-33, 51-58 and 97-107 of SEQ ID NO: 30 and the VL domain comprises residues 27-32, 50-52 and 89-97 of SEQ ID NO: 32.

4. The monoclonal antibody or antigen-binding fragment of claim 1, wherein the CDR sequences are CDR sequences determined by Kabat.

5. The monoclonal antibody or antigen-binding fragment of claim 4, wherein:
the VH domain comprises residues 31-37, 52-67 and 100-111 of SEQ ID NO: 2 and the VL domain comprises residues 24-34, 50-56 and 89-97 of SEQ ID NO: 4;
the VH domain comprises residues 30-34, 49-65 and 98-106 of SEQ ID NO: 6 and the VL domain comprises residues 24-34, 50-56 and 89-97 of SEQ ID NO: 8;
the VH domain comprises residues 22-26, 41-57 and 90-99 of SEQ ID NO: 10 and the VL domain comprises residues 24-34, 49-55 and 88-96 of SEQ ID NO: 12;
the VH domain comprises residues 30-35, 50-65 and 98-107 of SEQ ID NO: 14 and the VL domain comprises residues 24-34, 50-56 and 89-97 of SEQ ID NO: 16;
the VH domain comprises residues 31-35, 50-68 and 101-109 of SEQ ID NO: 18 and the VL domain comprises residues 24-33, 49-55 and 88-96 of SEQ ID NO: 20;
the VH domain comprises residues 31-36, 51-66 and 99-105 of SEQ ID NO: 22 and the VL domain comprises residues 24-33, 49-55 and 88-96 of SEQ ID NO: 24;
the VH domain comprises residues 31-35, 50-66 and 99-106 of SEQ ID NO: 26 and the VL domain comprises residues 24-34, 50-56 and 89-97 of SEQ ID NO: 28; or
the VH domain comprises residues 31-35, 50-66 and 99-107 of SEQ ID NO: 30 and the VL domain comprises residues 24-34, 50-56 and 89-97 of SEQ ID NO: 32.

6. The monoclonal antibody or antigen-binding fragment of claim 1, wherein the VH domain comprises the amino acid sequence of SEQ ID NO: 2, SEQ ID NO: 6, SEQ ID NO: 10, SEQ ID NO: 14, SEQ ID NO: 18, SEQ ID NO: 22, SEQ ID NO: 26 or SEQ ID NO: 30.

7. The monoclonal antibody or antigen-binding fragment of claim 1, wherein the VL domain comprises the amino acid sequence of SEQ ID NO: 4, SEQ ID NO: 8, SEQ ID NO: 12, SEQ ID NO: 16, SEQ ID NO: 20, SEQ ID NO: 24, SEQ ID NO: 28 or SEQ ID NO: 32.

8. The monoclonal antibody of claim 1, wherein the monoclonal antibody is an IgG.

9. The antigen-binding fragment of claim 1, wherein fragment comprises an Fab fragment, an Fab' fragment, an F(ab)'$_2$ fragment, a single chain variable fragment (scFv) or a disulfide stabilized variable fragment (dsFv).

10. The monoclonal antibody or antigen-binding fragment of claim 1, wherein the monoclonal antibody or antigen-binding fragment is a chimeric antibody comprising human and mouse amino acid sequence.

11. The monoclonal antibody or antigen-binding fragment of claim 1, wherein the monoclonal antibody or antigen-binding fragment is humanized.

12. A fusion protein comprising the monoclonal antibody or antigen-binding fragment of claim 1 and a heterologous protein.

13. An immunoconjugate comprising the monoclonal antibody or antigen-binding fragment of claim 1 and a detectable label.

14. A composition comprising the monoclonal antibody or antigen-binding fragment of claim 1 and a pharmaceutically acceptable carrier.

15. A composition comprising the monoclonal antibody or antigen-binding fragment of claim 1 conjugated to a microsphere.

16. The composition of claim 15, wherein the microsphere comprises a fluorophore.

17. The composition of claim 15, further comprising HRTV N protein bound to the monoclonal antibody or antigen-binding fragment.

18. A method of detecting HRTV-specific antibodies in a biological sample, comprising:
contacting the biological sample with the composition of claim 17 under conditions sufficient to allow binding of any HRTV-specific antibodies present in the biological sample to the HRTV N protein, thereby forming a microsphere immune complex;
- contacting the microsphere immune complex with a labelled secondary antibody; and
- detecting binding of the secondary antibody to the microsphere immune complex, thereby detecting HRTV-specific antibodies present in the biological sample.

19. The method of claim 18, wherein the method is a method of detecting HRTV-specific IgM antibodies and the secondary antibody is anti-human IgM; or the method is a method of detecting HRTV-specific IgG antibodies and the secondary antibody is anti-human IgG.

20. A method of detecting HRTV-specific antibodies in a biological sample, comprising:
- providing the monoclonal antibody or antigen-binding fragment of claim 1 bound to a solid support;
- contacting the antibody-bound solid support with a preparation comprising HRTV N protein under conditions sufficient for the HRTV N protein to bind the monoclonal antibody or antigen-binding fragment to form an antibody-antigen complex;

contacting the antibody-antigen complex with the biological sample to allow binding of any HRTV-specific antibodies present in the sample to the HRTV N protein, thereby forming an immune complex;

contacting the immune complex with a labelled secondary antibody; and detecting binding of the secondary antibody to the immune complex, thereby detecting HRTV-specific antibodies present in the biological sample.

21. A method of detecting HRTV-specific antibodies in a biological sample, comprising:

providing a secondary antibody bound to a solid support;

contacting the secondary antibody-bound solid support with the biological sample under conditions sufficient to allow binding of the secondary antibody to any HRTV-specific antibodies present in the biological sample, thereby forming antibody-antibody complexes;

contacting the antibody-antibody complexes with a preparation comprising HRTV N protein under conditions sufficient for the HRTV N protein to bind the HRTV-specific antibodies, thereby forming immune complexes;

contacting the immune complexes with the immunoconjugate of claim 13; and detecting binding of the immunoconjugate to the immune complexes, thereby detecting HRTV-specific antibodies in the biological sample.

22. The method of claim 21, wherein the biological sample comprises serum.

23. A method of detecting HRTV in an isolated cell or tissue, comprising:

contacting the cell or tissue with the monoclonal antibody or antigen binding fragment of claim 1; and detecting binding of the antibody to the cell or tissue, wherein an increase in binding of the antibody to the cell or tissue as compared to binding of the antibody to a control cell or tissue detects HRTV in the cell or tissue.

24. A method, comprising administering to a subject infected with HRTV the monoclonal antibody or antigen-binding fragment of claim 1.

* * * * *

SEQUENCE LISTING

<160> NUMBER OF SEQ ID NOS: 34

<210> SEQ ID NO 1
<211> LENGTH: 470
<212> TYPE: DNA
<213> ORGANISM: Artificial Sequence
<220> FEATURE:
<223> OTHER INFORMATION: Synthetic polynucleotide

<400> SEQUENCE: 1

```
caggttactc tgaaagagtc tggccctggg atattgcagc cctcccagac cctcagtctg    60
acttgttctt tctctgggtt ttcactgagc acttctggta tgagtgtagg ctggattcgt   120
cagccttcag ggaagggtct ggagtggctg gcacacattt ggtggaatga tgatatgtac   180
tataacccag ccctggaaag ccggctcaca atctccaagg atacctccaa caaccaggtt   240
ttcctcaaga tcgccagtgt ggtcactgca gatactgcca catactactg tgctcgaata   300
gccctaactg ggccctactg gtacttcgat gtctggggcg cagggaccac ggtcaccgtc   360
tcctcagcca aaacaacagc ccatcggtc tatccactgg ccctgtgtg tggagataca   420
actggctcct cggtgactct aggatgcctg gtcaaggcta gcatccgaat              470
```

<210> SEQ ID NO 2
<211> LENGTH: 152
<212> TYPE: PRT
<213> ORGANISM: Artificial Sequence
<220> FEATURE:
<223> OTHER INFORMATION: Synthetic polypeptide

<400> SEQUENCE: 2

```
Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Ala His Ile Trp Trp Asn Asp Asp Met Tyr Tyr Asn Pro Ala
    50                  55                  60

Leu Glu Ser Arg Leu Thr Ile Ser Lys Asp Thr Ser Asn Asn Gln Val
65                  70                  75                  80

Phe Leu Lys Ile Ala Ser Val Val Thr Ala Asp Thr Ala Thr Tyr Tyr
                85                  90                  95

Cys Ala Arg Ile Ala Leu Thr Gly Pro Tyr Trp Tyr Phe Asp Val Trp
            100                 105                 110

Gly Ala Gly Thr Thr Val Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys
145                 150
```

<210> SEQ ID NO 3
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 3

```
gacattgtga tgacccagac tccagcctcc ctatctgcat ctgtgggaga aactgtcacc    60
```

```
atcacatgtc gagcaagtga gaatatttac agttatttag catggtatca gcagaaacag      120
ggaaaatctc ctcagctcct ggtcaataat gcaaaaacct tagcagaagg tgtgccatca      180
aggttcagtg cagtggttc aggcacacag ttttctctga agatcaacag cctgcagcct      240
gaagattgtg ggaattatta ctgtcaacat cattatggca ctccgctcac gttcggtgct      300
gggaccaagc tggagctgaa a                                                321
```

<210> SEQ ID NO 4
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 4

```
Asp Ile Val Met Thr Gln Thr Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Asn Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Cys Gly Asn Tyr Tyr Cys Gln His His Tyr Gly Thr Pro Leu
                85                  90                  95

Thr Phe Gly Ala Gly Thr Lys Leu Glu Leu Lys
            100                 105
```

<210> SEQ ID NO 5
<211> LENGTH: 354
<212> TYPE: DNA
<213> ORGANISM: Artificial Sequence
<220> FEATURE:
<223> OTHER INFORMATION: Synthetic polynucleotide

<400> SEQUENCE: 5

```
gaagtgcagc tggaggagtc tggggctgaa ctggtgaggt ctggggcctc actgaagatg      60
tcctgcaagg cttctggcta cacatttacc agttacaatc tgcactgggt taagcagaca      120
ccaggacagg gcctggaatg gattggatat attttttcctg gaaatggtgg tactgcctac      180
aatgagaagt tcaagggcaa ggccacattg actgcagaca catcctcctc cacagcctac      240
atgcagatca gcagcctgac atctgaggac tctgcggtct atttctgtgc aagagggggc      300
ccttactatg ctttggacta ctggggtcaa ggaacctcag tcaccgtctc ctca            354
```

<210> SEQ ID NO 6
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 6

```
Val Lys Leu Glu Glu Ser Gly Ala Glu Leu Val Arg Ser Gly Ala Ser
1               5                   10                  15

Leu Lys Met Ser Cys Lys Ala Ser Gly Tyr Thr Phe Thr Ser Tyr Asn
            20                  25                  30
```

Leu His Trp Val Lys Gln Thr Pro Gly Gln Gly Leu Glu Trp Ile Gly
        35                  40                  45

Tyr Ile Phe Pro Gly Asn Gly Gly Thr Ala Tyr Asn Glu Lys Phe Lys
            50                  55                  60

Gly Lys Ala Thr Leu Thr Ala Asp Thr Ser Ser Thr Ala Tyr Met
65                  70                  75                  80

Gln Ile Ser Ser Leu Thr Ser Glu Asp Ser Ala Val Tyr Phe Cys Ala
                85                  90                  95

Arg Gly Gly Pro Tyr Tyr Ala Leu Asp Tyr Trp Gly Gln Gly Thr Ser
                100                 105                 110

Val Thr Val Ser Ser
        115

<210> SEQ ID NO 7
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 7
gacattgtga tgacccagtc tccagcctcc ctatctgcat ctgtgggaga aactgtcacc      60
atcacatgtc gaacaagtgg gaatattcac acttatttag catggtatca gcacaaacag     120
ggaaaatctc ctcagctcct ggtctattat gcaaaaacct agcagatggg gtgccatca     180 aggttcagtg gcagtggatc aggaacacaa tattctctca agatcaacag cctgcagcct     240
gaagattttg ggagttatta ctgtcaacat ttttggagta atcctcggac gttcggtgga     300
ggcaccaagc tggaaatcaa a                                               321

<210> SEQ ID NO 8
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 8

Asp Ile Val Met Thr Gln Ser Pro Ala Ser Leu Ser Ala Ser Val Gly
1               5                   10                  15

Glu Thr Val Thr Ile Thr Cys Arg Thr Ser Gly Asn Ile His Thr Tyr
            20                  25                  30

Leu Ala Trp Tyr Gln His Lys Gln Gly Lys Ser Pro Gln Leu Leu Val
        35                  40                  45

Tyr Tyr Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Asn Pro Arg
                85                  90                  95

Thr Phe Gly Gly Gly Thr Lys Leu Glu Ile Lys Arg Ala Asp Ala Ala
                100                 105                 110

Pro Thr Val Ser
        115

<210> SEQ ID NO 9
<211> LENGTH: 330
<212> TYPE: DNA

<213> ORGANISM: Artificial Sequence
<220> FEATURE:
<223> OTHER INFORMATION: Synthetic polynucleotide

<400> SEQUENCE: 9

```
gaactggcaa gacctggggc ttcagtgaag ttgtcctgca aggcttctgg ctacaccttt      60
actaattact atatgcagtg gataaaacag cggcctggac agggtctgga gtggattggg     120
gctgtttatc ctggagatgg tgatactagg tacactcaga agttcaaggg caaggcctca     180
ttgactgcag ataaatcctc caccacagcc tatatgcaac tcagcagctt ggcatctgag     240
gactctgcgg tctattactg tacaaggggga gattacgagg gaacctggtt tacttactgg     300
ggccaaggga ctctggtcac tgtctctgca                                       330
```

<210> SEQ ID NO 10
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 10

```
Glu Leu Ala Arg Pro Gly Ala Ser Val Lys Leu Ser Cys Lys Ala Ser
1               5                   10                  15
Gly Tyr Thr Phe Thr Asn Tyr Tyr Met Gln Trp Ile Lys Gln Arg Pro
            20                  25                  30
Gly Gln Gly Leu Glu Trp Ile Gly Ala Val Tyr Pro Gly Asp Gly Asp
        35                  40                  45
Thr Arg Tyr Thr Gln Lys Phe Lys Gly Lys Ala Ser Leu Thr Ala Asp
    50                  55                  60
Lys Ser Ser Thr Thr Ala Tyr Met Gln Leu Ser Ser Leu Ala Ser Glu
65                  70                  75                  80
Asp Ser Ala Val Tyr Tyr Cys Thr Arg Gly Asp Tyr Glu Gly Thr Trp
                85                  90                  95
Phe Thr Tyr Trp Gly Gln Gly Thr Leu Val Thr Val Ser Ala
            100                 105                 110
```

<210> SEQ ID NO 11
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 11

```
gatattgtga tgacccagac tccagcaatc atgtctgcat ctccagggga gaaggtcacc      60
atgacctgca gtgccagctc aagtgtaagt tacatgcact ggtaccagca gaagtcaggc     120
acctccccca aaagatggat gtatgacaca tccaaactgg cttctggagt ccctggtcgc     180
ttcagtggca gtgggtctgg gaccacttac tctctcacaa tcagcaccat ggaggctgaa     240
gatgctgcca cctattactg ccagcagtgg agtagtaacc cacccacgtt cggggggggg     300
accaagctgg aaataaaa                                                    318
```

<210> SEQ ID NO 12
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 12

Asp Ile Val Met Thr Gln Thr Thr Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Met Tyr
        35                  40                  45

Asp Thr Ser Lys Leu Ala Ser Gly Val Pro Arg Phe Ser Gly Ser
    50                  55                  60

Gly Ser Gly Thr Thr Tyr Ser Leu Thr Ile Ser Thr Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 13
<211> LENGTH: 354
<212> TYPE: DNA
<213> ORGANISM: Artificial Sequence
<220> FEATURE:
<223> OTHER INFORMATION: Synthetic polynucleotide

<400> SEQUENCE: 13
gtgcagctgc aggagtcggg acctggcctc gtgaaacctt cgcagcctct gtctctcacc      60
tgctctgtca ctggctactc cattaccagt gcttattact ggaactggat ccggcagttt     120
ccaggaaaca aactggaatg gatgggatac ataacctacg acggtaccaa taactacaac     180
ccatctctca aaatcgaat ctccatcact cgtgacacat ctaagaacca gttttttcctg    240 aagttgaatt ctgtgactac tgaggacaca gcttcatatt actgtgcaag agatgttgct     300
acggtcggtg ctatggacta ctggggtcaa ggaacctcag tcaccgtctc ctca           354

<210> SEQ ID NO 14
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 14

Val Gln Leu Gln Glu Ser Gly Pro Gly Leu Val Lys Pro Ser Gln Pro
1               5                   10                  15

Leu Ser Leu Thr Cys Ser Val Thr Gly Tyr Ser Ile Thr Ser Ala Tyr
            20                  25                  30

Tyr Trp Asn Trp Ile Arg Gln Phe Pro Gly Asn Lys Leu Glu Trp Met
        35                  40                  45

Gly Tyr Ile Thr Tyr Asp Gly Thr Asn Asn Tyr Asn Pro Ser Leu Lys
    50                  55                  60

Asn Arg Ile Ser Ile Thr Arg Asp Thr Ser Lys Asn Gln Phe Phe Leu
65                  70                  75                  80

Lys Leu Asn Ser Val Thr Thr Glu Asp Thr Ala Ser Tyr Tyr Cys Ala
                85                  90                  95

Arg Asp Val Ala Thr Val Gly Ala Met Asp Tyr Trp Gly Gln Gly Thr
            100                 105                 110

Ser Val Thr Val Ser Ser
            115

<210> SEQ ID NO 15
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 15

```
agtattgtga tgacccagac tcccaaattc ctgcttgtat cagcaggaga cagggttacc      60
ataacctgca aggccagtca gagtgtgagt aatgatgtag cttggtacca acagaagcca     120
gggcagtctc ctaaactgct gatatacttt gcatccaatc gctacactgg agtccctgat     180
cgcttcactg gcagtggata tgggacggat ttcactttca ccatcagcac tgtgctggct     240
gaagacctgg cactttattt ctgtcagcag gattatagct ctcctcggac gttcggtgga     300
ggcaccaaac tggaagtcaa a                                               321
```

<210> SEQ ID NO 16
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 16

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Phe Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Leu Ala
65                  70                  75                  80

Glu Asp Leu Ala Leu Tyr Phe Cys Gln Gln Asp Tyr Ser Ser Pro Arg
                85                  90                  95

Thr Phe Gly Gly Gly Thr Lys Leu Glu Val Lys
            100                 105
```

<210> SEQ ID NO 17
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 17

```
gaggtgcagc tggaggagtc aggaggaggc ttggtgcaac ctggaggatc catgaaactc      60
tcctgtgttg cctctggatt cactttcagt aactactgga tgaactgggt ccgccagtct     120
ccagagaagg ggcttgagtg ggttgctgaa gttagattga attctaataa ttatgcaaca     180
cattatgcgg agtctgtgaa agggaggttc accatctcaa gagatgattc caaaagtagt     240
gtctacctgc aaatgagcaa cttaagatct gaagacactg gcatttatta ttgttccacc     300
gattattacg ctatgctat ggactactgg ggtcaaggaa cctcagtcac cgtctcctca     360
```

<210> SEQ ID NO 18
<211> LENGTH: 120
<212> TYPE: PRT

<213> ORGANISM: Artificial Sequence
<220> FEATURE:
<223> OTHER INFORMATION: Synthetic polypeptide

<400> SEQUENCE: 18

```
Glu Val Gln Leu Glu Glu Ser Gly Gly Gly Leu Val Gln Pro Gly Gly
1               5                   10                  15
Ser Met Lys Leu Ser Cys Val Ala Ser Gly Phe Thr Phe Ser Asn Tyr
            20                  25                  30
Trp Met Asn Trp Val Arg Gln Ser Pro Glu Lys Gly Leu Glu Trp Val
        35                  40                  45
Ala Glu Val Arg Leu Asn Ser Asn Asn Tyr Ala Thr His Tyr Ala Glu
    50                  55                  60
Ser Val Lys Gly Arg Phe Thr Ile Ser Arg Asp Asp Ser Lys Ser Ser
65                  70                  75                  80
Val Tyr Leu Gln Met Ser Asn Leu Arg Ser Glu Asp Thr Gly Ile Tyr
                85                  90                  95
Tyr Cys Ser Thr Asp Tyr Tyr Gly Tyr Ala Met Asp Tyr Trp Gly Gln
            100                 105                 110
Gly Thr Ser Val Thr Val Ser Ser
        115                 120
```

<210> SEQ ID NO 19
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 19

```
gatattgtga tgacccagac tccatcaatc atgtctgcat ctccagggga gaaggtcacc      60
ataacctgca gtgccagctc taatgtaaat tacatgcact ggttccagca gaagccaggc    120
acttctccca aactctggat ttatagcaca tccaacctgg cttctggagt ccctgctcgc    180
ttcagtggca gtggatctgg gacctcttac tctctcacaa tcagccgaat ggaggctgaa    240
gatgctgcca cttattactg ccagcaaagg agtaattacc cacccacgtt cggtgctggg    300
accaagctgg agctgaaa                                                  318
```

<210> SEQ ID NO 20
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 20

```
Asp Ile Val Met Thr Gln Thr Pro Ser Ile Met Ser Ala Ser Pro Gly
1               5                   10                  15
Glu Lys Val Thr Ile Thr Cys Ser Ala Ser Ser Asn Val Asn Tyr Met
            20                  25                  30
His Trp Phe Gln Gln Lys Pro Gly Thr Ser Pro Lys Leu Trp Ile Tyr
        35                  40                  45
Ser Thr Ser Asn Leu Ala Ser Gly Val Pro Ala Arg Phe Ser Gly Ser
    50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Arg Ser Asn Tyr Pro Pro Thr
                85                  90                  95
```

Phe Gly Ala Gly Thr Lys Leu Glu Leu Lys
            100                 105

<210> SEQ ID NO 21
<211> LENGTH: 348
<212> TYPE: DNA
<213> ORGANISM: Artificial Sequence
<220> FEATURE:
<223> OTHER INFORMATION: Synthetic polynucleotide

<400> SEQUENCE: 21
gaggttcagc tggaggagtc aggacctgac ctggtgaaac cttctcagtc actttcactc      60
acctgcactg tcactggctt ctccatcacc agtggttata gttggcactg gatccggcaa    120
tttccaggaa acaaactgga atggatgggc tacatacact tcagtggtag cacgaactac    180
aacccatctc tcaaaagtcg aatctctatc actcgagaca catccaagaa ccagttcttc    240
ctgcagttga gttctgtgac tactgacgac acaggcacat attactgtgc aagagatctg    300
actgggatta ctcctgggg ccaaggcacc actctcacag tctcctca                  348

<210> SEQ ID NO 22
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 22

Glu Val Gln Leu Glu Glu Ser Gly Pro Asp Leu Val Lys Pro Ser Gln
1               5                   10                  15

Ser Leu Ser Leu Thr Cys Thr Val Thr Gly Phe Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Phe Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Ser Ser Val Thr Thr Asp Asp Thr Gly Thr Tyr Tyr Cys
                85                  90                  95

Ala Arg Asp Leu Thr Gly Ile Thr Pro Gly Gly Gln Gly Thr Thr Leu
            100                 105                 110

Thr Val Ser Ser
        115

<210> SEQ ID NO 23
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 23
gatattgtga tgacacagac tccagcaatc atgtctgcat ctccagggga gaaggtcacc      60
atatcctgca gtgccagctc aagtgtaagt tacatgtact ggttccagca gaagccagga    120
tcctccccca aaccctggat ttatcgcaca tccaacctgg cttctggagt ccctgctcgc    180
ttcagtggca gtgggtctgg gacctcttac tctgtcacaa tcagcagcat ggaggctgaa    240
gatgctgcca cttattactg ccagcagtat catagttacc cactcacgtt cggtgctggg    300
accaagctgg agctgaaa                                                    318

<210> SEQ ID NO 24
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 24

Asp Ile Val Met Thr Gln Thr Pro Ala Ile Met Ser Ala Ser Pro Gly
1               5                   10                  15

Glu Lys Val Thr Ile Ser Cys Ser Ala Ser Ser Val Ser Tyr Met Tyr
            20                  25                  30

Tyr Trp Phe Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Val Thr Ile Ser Ser Met Glu Ala Glu
65                  70                  75                  80

Asp Ala Ala Thr Tyr Tyr Cys Gln Gln Tyr His Ser Tyr Pro Leu Thr
                85                  90                  95

Phe Gly Ala Gly Thr Lys Leu Glu Leu Lys
            100                 105

<210> SEQ ID NO 25
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 25
gaggtccagc tgcaacagtc tggacctgac ctggtgaagc ctggagcttc aatgaagata      60
tcctgcaagg cttctggtta ctcattcact gcctacacca tgaactgggt gaagcagagc     120
catggaaaga accttgagtg gattggactt attagtcctt acaatggtgg tactagttac     180
aaccagaagt tcaagggcaa ggccacatta actgtagaca agtcatccag cacagcctac     240
atggagctcc tcagtctgac atctgaggac tctgcagtct attactgtgc aagacagatc     300
gggccttact ttgaccattg gggccaaggc accactctca cagtctcctc a               351

<210> SEQ ID NO 26
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 26

Glu Val Gln Leu Gln Gln Ser Gly Pro Asp Leu Val Lys Pro Gly Ala
1               5                   10                  15

Ser Met Lys Ile Ser Cys Lys Ala Ser Gly Tyr Ser Phe Thr Ala Tyr
            20                  25                  30

Thr Met Asn Trp Val Lys Gln Ser His Gly Lys Asn Leu Glu Trp Ile
        35                  40                  45

Gly Leu Ile Ser Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr

Met Glu Leu Leu Ser Leu Thr Ser Glu Asp Ser Ala Val Tyr Tyr Cys
65                  70                  75                  80

Ala Arg Gln Ile Gly Pro Tyr Phe Asp His Trp Gly Gln Gly Thr Thr
            85                  90                  95

Leu Thr Val Ser Ser
        100                 105                 110

115

<210> SEQ ID NO 27
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 27
gacattgtga tgacccagac tccatcttcc atgtatgcat ctctaggaga gagagtcact    60
atcacttgca aggcgagtca ggacattaaa agctctttta gttggttcca gcagaaacca   120
gggaaatctc ctaagaccct gatctatcgt gcaagcagat tggtagatgg ggtcccatca   180
aggttcagtg gcagtggatc tgggcaagat tcttctctca ccatcagcag cctggagtat   240
gaagatatgg gaatttatta ttgtctacag tgtgatgagt ttccgtacac gttcggaggg   300
gggaccaagc tggaaataaa a                                             321

<210> SEQ ID NO 28
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 28

Asp Ile Val Met Thr Gln Thr Thr Pro Ser Ser Met Tyr Ala Ser Leu
1               5                   10                  15

Gly Glu Arg Val Thr Ile Thr Cys Lys Ala Ser Gln Asp Ile Lys Ser
            20                  25                  30

Ser Phe Ser Trp Phe Gln Gln Lys Pro Gly Lys Ser Pro Lys Thr Leu
        35                  40                  45

Ile Tyr Arg Ala Ser Arg Leu Val Asp Gly Val Pro Ser Arg Phe Ser
    50                  55                  60

Gly Ser Gly Ser Gly Gln Asp Ser Ser Leu Thr Ile Ser Ser Leu Glu
65                  70                  75                  80

Tyr Glu Asp Met Gly Ile Tyr Tyr Cys Leu Gln Cys Asp Glu Phe Pro
                85                  90                  95

Tyr Thr Phe Gly Gly Gly Thr Lys Leu Glu Ile Lys
            100                 105

<210> SEQ ID NO 29
<211> LENGTH: 355
<212> TYPE: DNA
<213> ORGANISM: Artificial Sequence
<220> FEATURE:
<223> OTHER INFORMATION: Synthetic polynucleotide

<400> SEQUENCE: 29
caggcttatc tacagcagtc tggggctgaa ctggtgaggt ctggggcctc actgaagatg    60
tcctgcaagg cttctggcta cacatttacc agttacaatc tgcactgggt taagcagaca   120
ccaggacagg gcctggaatg gattggatat atttttcctg gaaatggtgg tactgcctac   180

```
aatgagaagt tcaagggcaa ggccacattg actgcagaca catcctcctc cacagcctac    240
atgcagatca gcagcctgac atctgaggac tctgcggtct atttctgtgc aagaggggc     300 ccttactatg ctttggacta ctggggtcaa ggaacctcag tcaccgtctc ctcag         355
```

<210> SEQ ID NO 30
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 30

```
Gln Ala Tyr Leu Gln Gln Ser Gly Ala Glu Leu Val Arg Ser Gly Ala
1               5                   10                  15

Ser Leu Lys Met Ser Cys Lys Ala Ser Gly Tyr Thr Phe Thr Ser Tyr
            20                  25                  30

Asn Leu His Trp Val Lys Gln Thr Pro Gly Gln Gly Leu Glu Trp Ile
        35                  40                  45

Gly Tyr Ile Phe Pro Gly Asn Gly Gly Thr Ala Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Gly Pro Tyr Tyr Ala Leu Asp Tyr Trp Gly Gln Gly Thr
            100                 105                 110

Ser Val Thr Val Ser Ser
        115
```

<210> SEQ ID NO 31
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 31

```
gacatccaga tgactcagtc tccagcctcc ctatctgcat ctgtgggaga aactgtcacc    60
atcacatgtc gaacaagtgg gaatattcac acttatttag catggtatca gcacaaacag    120
ggaaaatctc ctcagctcct ggtctattat gcaaaaacct tagcagatgg tgtgccatca    180
aggttcagtg gcagtggatc aggaacacaa tattctctca agatcaacag cctgcagcct    240
gaagattttg ggagttatta ctgtcaacat ttttggagta atcctcggac gttcggtgga    300
ggcaccaagc tggaaatcaa a                                              321
```

<210> SEQ ID NO 32
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 32

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Gly Asn Ile His Thr Tyr
            20                  25                  30
```

```
Leu Ala Trp Tyr Gln His Lys Gln Gly Lys Ser Pro Gln Leu Leu Val
             35                  40                  45
Tyr Tyr Ala Lys Thr Leu Ala Asp Gly Val Pro Ser Arg Phe Ser Gly
 50                  55                  60
Ser Gly Ser Gly Thr Gln Tyr Ser Leu Lys Ile Asn Ser Leu Gln Pro
 65                  70                  75                  80
Glu Asp Phe Gly Ser Tyr Tyr Cys Gln His Phe Trp Ser Asn Pro Arg
                 85                  90                  95
Thr Phe Gly Gly Gly Thr Lys Leu Glu Ile Lys
                100                 105
```

<210> SEQ ID NO 33
<211> LENGTH: 336
<212> TYPE: DNA
<213> ORGANISM: Artificial Sequence
<220> FEATURE:
<223> OTHER INFORMATION: Synthetic polynucleotide

<400> SEQUENCE: 33

```
gatattgtga tgacacagac tccactctcc ctgcctgtca gtcttggaga tcaagcctcc      60
atctcttgca gatctagtca gagcattgta catagtaatg aaacaccta tttagaatgg     120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
tggacgttcg gtggaggcac caagctggaa atcaaa                              336
```

<210> SEQ ID NO 34
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 34

```
Asp Ile Val Met Thr Gln Thr Pro Leu Ser Leu Pro Val Ser Leu Gly
 1               5                  10                  15
Asp Gln Ala Ser Ile Ser Cys Arg Ser Ser Gln Ser Ile Val His Ser
             20                  25                  30
Asn Gly Asn Thr Tyr Leu Glu Trp Tyr Leu Gln Lys Pro Gly Gln Ser
         35                  40                  45
Pro Lys Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Tyr Cys Phe Gln Gly
                 85                  90                  95
Ser His Val Pro Trp Thr Phe Gly Gly Gly Thr Lys Leu Glu Ile Lys
                100                 105                 110
```